(12) United States Patent
Wang et al.

(10) Patent No.: US 12,251,193 B2
(45) Date of Patent: Mar. 18, 2025

(54) SCANNING BASED THZ NEARFIELD IMAGING DEVICE

(71) Applicant: National Tsing Hua University, Hsinchu (TW)

(72) Inventors: Wei-Chih Wang, Sammamish, WA (US); Karthikraj Muthuramalingam, Hsinchu (TW); Fiona Marie Wang, Seattle, WA (US)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 416 days.

(21) Appl. No.: 17/692,159

(22) Filed: Mar. 10, 2022

(65) Prior Publication Data

US 2023/0284907 A1   Sep. 14, 2023

(51) Int. Cl.
| | |
|---|---|
| *A61B 5/00* | (2006.01) |
| *A61B 5/0507* | (2021.01) |
| *G01J 5/04* | (2006.01) |
| *G01J 5/00* | (2022.01) |

(52) U.S. Cl.
CPC ............ *A61B 5/0088* (2013.01); *G01J 5/047* (2013.01); *A61B 5/0507* (2013.01); *G01J 2005/0077* (2013.01)

(58) Field of Classification Search
CPC ... A61B 5/0088; A61B 5/0507; A61B 5/4842; G01J 2005/0077; G01J 3/42; G01J 5/047; G01N 21/3581; G01N 21/3586
See application file for complete search history.

(56) References Cited

U.S. PATENT DOCUMENTS

| | | | |
|---|---|---|---|
| 3,949,229 A | | 4/1976 | Albert |
| 10,288,979 B1 | * | 5/2019 | Wang .................... G02F 1/29 |
| 2005/0100866 A1 | * | 5/2005 | Arnone ................. A61B 5/417 |
| | | | 433/29 |
| 2015/0316475 A1 | | 11/2015 | Rahman et al. |

(Continued)

FOREIGN PATENT DOCUMENTS

| | | | | |
|---|---|---|---|---|
| CN | 104013387 A | | 9/2014 | |
| CN | 114039201 A | * | 2/2022 | ............... H01Q 1/36 |
| KR | 1020190004511 A | | 1/2019 | |

OTHER PUBLICATIONS

Adam, A.J.L. "Review of Near-Field Terahertz Measurement Methods and Their Applications. How to Achieve Sub-Wavelength Resolution at THz Frequencies". J Infrared Milli Terahz Waves (2011) 32:976-1019 (Year: 2011).*

(Continued)

*Primary Examiner* — Colin T. Sakamoto
*Assistant Examiner* — Milton Truong
(74) *Attorney, Agent, or Firm* — HSML P. C.

(57) ABSTRACT

Provided is a simple, portable, real-time, and in vivo THz imaging device for imaging a target, e.g., a tooth in the subject. Moreover, the scanning based THz imaging device is much sufficiently sensitive as compared with the common X-ray imaging device. Therefore, the scanning based THz imaging device has the potential to operate in the density for early detection problems such as dental caries or demineralization of the enamel in the teeth. Also provided is a method for diagnosing or imaging the target in the subject by using the scanning based THz imaging device of the present disclosure.

24 Claims, 22 Drawing Sheets

(56) References Cited

U.S. PATENT DOCUMENTS

2020/0292449 A1* 9/2020 Nebel .................... G01N 21/89
2021/0328550 A1* 10/2021 Asada .................... H01L 29/88

OTHER PUBLICATIONS

Nguyen, T.D et al. "Concentration of terahertz radiation through a conically tapered aperture". Optics Express 18:25441-25448 (2010) (Year: 2010).*

Allford, C.P. et al. "Strain Compensated InGaAs/AlAs Triple Barrier Resonant Tunneling Structures for THz Applications". IEEE Transactions On Terahertz Science and Technology, 7:772-779 (2017) (Year: 2017).*

Miyamoto, D. et al. "The fiber-optic imaging and manipulation of neural activity during animal behavior". Neuroscience Research 103 (2016) 1-9 (Year: 2016).*

Zhu, Y. et al. "A dual handheld SWIR transillumination/reflectance probe for imaging lesions on tooth occlusal and proximal surfaces". Proc SPIE Int Soc Opt Eng. Feb. 2020 ; 11217 (Year: 2020).*

International Search Report and Written Opinion issued in PCT/US2022/019855, dated Dec. 1, 2022, 9 pages provided.

* cited by examiner

SCANNING BASED THZ NEARFIELD IMAGING DEVICE

TECHNICAL FIELD

The present disclosure relates to an imaging device, and more particularly to a scanning based THz imaging device for biomedical imaging.

DESCRIPTION OF RELATED ART

Terahertz (THz) science and technology have been studied with great interest among the researchers for the last two decades. The THz spectrum gap between gap between the millimeter-wave and infrared is the last part of the EM-wave spectrum that needs to be explored for potential disclosures. And due to the recent advancements in the THz sources and detectors, the THz systems are now slowly transforming from laboratory level to commercial systems.

The common imaging practice in dentistry is the X-ray imaging which is not only harmful to the patients but also the equipment is bulky and expensive. The conventional dental imaging techniques such as X-ray and infrared luminescence imaging methods are not sufficiently sensitive to detect the early stages of dental caries to prevent in advance. Moreover, X-ray imaging is related to a stage in the disease processing or operating and certainly not recommended by the doctors for the early stage determination of dental caries.

Unlike X-rays, THz rays have less ionization energy thus safe to use in the biomedical imaging disclosures where humans are involved. The X-ray and the THz images of the human tooth are also compared, and it proves that with the sufficient improvements in the resolution of THz image, the terahertz systems have the potential to operate in the dentistry for early detection of dental problems. Terahertz rays have unique dielectric properties in metal and dental tissue, which makes it a safer and easier way for diagnosing even a very smaller gap during the metal filling inside the teeth on the surgery itself.

Although there have been few studies before proved the feasibility of THz imaging of human teeth, it still exists many significant physical and technical problems in developing a clinical level prototype for monitoring dental caries in the in-vivo step. Currently, there is no commercial device or in-vivo imaging clinical prototype that has been demonstrated. Foremost limitations in transforming the laboratory-level THz imaging devices into the commercial disclosures are the bulky and complex configurations, movable mechanical components, and expensive femtosecond lasers. The THz pulsed imaging is usually performed using the THz time-domain spectroscopy (THz-TDS) which requires a mechanical delay stage and therefore making it difficult to integrate into a portable system.

Therefore, a simple, portable, real-time, and in-vivo THz imaging device is highly desirable in dentistry for early and quick diagnosis of dental problems in a faster and much safer way.

SUMMARY

In view of the foregoing, the present disclosure provides a simple and portable THz imaging systems for both industrial and biomedical imaging.

In at least one embodiment of the present disclosure, the scanning based THz imaging device comprises a THz emitter for emitting a terahertz signal, a generator coupled with the THz emitter and configured for inducing the THz emitter to emit the terahertz signal, a receiver for receiving the terahertz signal.

In at least one embodiment of the present disclosure, the THz emitter of the scanning based THz imaging device comprises: a first cover, a first taper structure disposed in the first cover and having a distal end and a proximal end opposed to the distal end, a THz source disposed in the first cover and covered by the first taper structure to guide and generate a focused near field beam profile at the distal end of the first taper structure, and a beam deflector module coupled to the first cover. In some embodiments, the THz source is covered inside by the taper structure.

In at least one embodiment of the present disclosure, the generator of the scanning based THz imaging device is coupled with the THz emitter and configured for inducing the THz emitter to emit the terahertz signal.

In at least one embodiment of the present disclosure, the receiver of the scanning based THz imaging device comprises: a second cover, a second taper structure disposed in the second cover, and a THz detector disposed in the second cover and covered by the second taper structure. In some embodiments, the THz detector is covered inside by the taper structure.

In at least one embodiment of the present disclosure, the THz source comprises a RTD with an emitter and a collector, a resonator antenna electrically connected to the emitter and the collector of the RTD, and a radiator antenna disposed over the resonator antenna. In some embodiments, the RTD is a TBRTD or a multi-barrier RTD comprising a AIAs/InGaAS/AIAs layer, and this structure allows drastic improvement in the overall DC-RF conversion efficiency and smaller peak current-voltage.

In at least one embodiment of the present disclosure, a THz source has a radiator antenna. In some embodiments, the radiator antenna structure of the THz source is a spiral-antenna structure or any broadband antenna. In some embodiments, the radiator antenna structure of the THz source is a tunable fractal antenna structure, wherein frequency shift either is changed by its reconfiguration of its fractal pattern or by a voltage induced dielectric constant change in the antenna, where a much more continuous and infinitesimal frequency change can be achieved.

In at least one embodiment of the present disclosure, the first taper structure of a scanning based THz imaging device has an air-core part, an emitting aperture, and an entry aperture. In some embodiments, the air-core part has an inner wall coated with a material of metal to guide and generate focused near field beam profile at the exit of the taper end, and this nearfield operation allows the spatial image resolution to go beyond diffraction limit and further enhance the overall image resolution. In some embodiments, the emitting aperture of the first taper structure is cut with a certain angle to increase a deflection angle.

In at least one embodiment of the present disclosure, the beam deflector module is disposed at the emitting aperture of the taper structure and configured for the terahertz signal to transmit.

In at least one embodiment of the present disclosure, the beam deflector module is fabricated on a curved surface for focusing and deflecting the terahertz signal, and the beam deflector module is disposed at the emitting aperture of the first taper structure.

In at least one embodiment of the present disclosure, the beam deflector module is disposed at the entry aperture of the first taper structure and configured to deflect the terahertz signal emitted from the THz emitter and to enter the taper structure.

In at least one embodiment of the present disclosure, the beam deflector module comprises an electro-optic beam deflector or a galvo-mirror.

In at least one embodiment of the present disclosure, the beam deflector module is a physical terahertz fishnet metamaterial prism having a stacked fishnet structure.

In at least one embodiment of the present disclosure, a beam deflector module is a flat terahertz fishnet metamaterial prism having an array of a signal layer terahertz fishnet metamaterial structure. In some embodiments, the terahertz fishnet metamaterial structure comprises a first layer and a second layer opposed to the first layer. In some embodiments, the array of single layer terahertz fishnet metamaterial structure comprises a plurality of droplets disposed between the first layer and the second layer to form a plurality droplet layers. In some embodiments, the droplets are composed of a liquid crystal material and a size of the droplets is controlled by ultraviolet radiation to form a refractive index gradient.

In at least one embodiment of the present disclosure, a beam deflector module is an actively-controlled metamaterial lens for transforming functions between focusing function, diverging function, and collimating function by altering an applied voltage.

In at least one embodiment of the present disclosure, a scanning based THz imaging device further comprises a connector for detachably connecting a THz emitter to the receiver and separating the THz emitter from the receiver with a distance. In some embodiments, the distance between the THz emitter and the receiver is adjusted by the connector to allow reconstructing images of the target with different size.

The present disclosure also provides a method for diagnosing a disease, disorder, or condition of a subject, comprising: providing the scanning based THz imaging device of the present disclosure; emitting a terahertz signal from a THz emitter to a surface of the target in the subject in need thereof; receiving the terahertz signal reflected from the surface of the target by a receiver; and diagnosing a condition of the surface of the target by analyzing the received terahertz signal. In some embodiments, the method further comprises reconstructing an image of the target.

In at least one embodiment of the present disclosure the target may be, but not limited to, a soft tissue (e.g., skins), a hard tissue (e.g., bones), an enamel, dental tubules, nerves, blood vessels of the subject. In some embodiments, the target may be dielectric and has no water content, e.g., teeth or bones, but the present disclosure is not limited thereto. In some embodiments, the target is a tooth, and the surface is an enamel surface of the tooth.

In at least one embodiments of the present disclosure, the disease, disorder, or condition of a subject may be, but not limited to, dental caries (especially an early stage of dental caries), demineralization of the tooth structure (e.g., enamel in the teeth), peri-implantitis, periodontal disease, gingivitis, a curing process of dental composites, a lesion in the oral structure, or dental abnormalities. The human dental enamel is transparent in 0.4 to 0.55 THz, so the cavity or enamel demineralization of a tooth can be monitored at the initial stage itself. However, the limitation arises from the THz source and detector. Some embodiments of the present disclosure provide a THz-scanner using the air-side emitting RTD and beam scanning device suitable for the dental imaging.

In at least one embodiments of the present disclosure, the disease, disorder, or condition of a subject may be, but not limited to, burns, edema, or cancer. In some embodiments, the burns are second degree or higher burns. In some embodiments, the cancer may be, but not limited to, a skin cancer, bone cancer, oral cancer, oral lymphoma, mucosal melanoma, oral sarcomas, oral squamous cell carcinoma, or adenocarcinoma. Cancer detection or cancer classification is one of the predominant biomedical applications; however, the currently available THz-camera is not just too expensive but also the resolution is poor. Hence, the transceiver design of the present disclosure may be assembled in an array using the COMS technology and opening the possibilities of low-cost terahertz bio-medical imaging, such that the non-destructive cancer imaging by THz for cancer diagnosis can be achieved.

In some embodiments, the terahertz radiation of the target with caries is greater than the target without caries.

In some embodiments, the target is a skin margin with low refractive index and absorbance of terahertz hertz.

In some embodiments, an absorption of terahertz radiation by an affected tissue is greater than the absorption of terahertz radiation by a healthy tissue.

In some embodiments, the demineralized enamel shows an increasing of terahertz transmission signal compared to healthy tooth structure.

In some embodiment, the margin of cancer or tumor or less dense tissue compared to healthy tissue may be detected as visible terahertz imaging in early stage, middle stage or late stage of a target tissue.

The present disclosure further provides a method for imaging a target in a subject, comprising: providing the scanning based THz imaging device of the present disclosure; emitting a terahertz signal from a THz emitter to a surface of the target in the subject in need thereof; receiving the terahertz signal reflected from the surface of the target by a receiver; and reconstructing an image of the subject by the received terahertz signal. In some embodiments, the target is dielectric and has no water.

In the portable THz imaging device for diagnosing the conditions of a subject as describe in the present disclosure, the THz imaging device may be manufactured as a simple, portable, real-time, and in vivo THz imaging device for imaging dental tissues. Moreover, the portable THz imaging device is much sufficiently sensitive to detect the early stages of dental caries as comparing with the common X-ray. As such, the THz imaging device of the present disclosure may operate in the density for early detection of dental problems such as imaging enamel thickness at high resolution.

BRIEF DESCRIPTION OF THE DRAWINGS

The present disclosure can be more fully understood by reading the following descriptions of the embodiments, with reference made to the accompanying drawings.

DETAILED DESCRIPTION OF THE EMBODIMENTS

Figure 1:
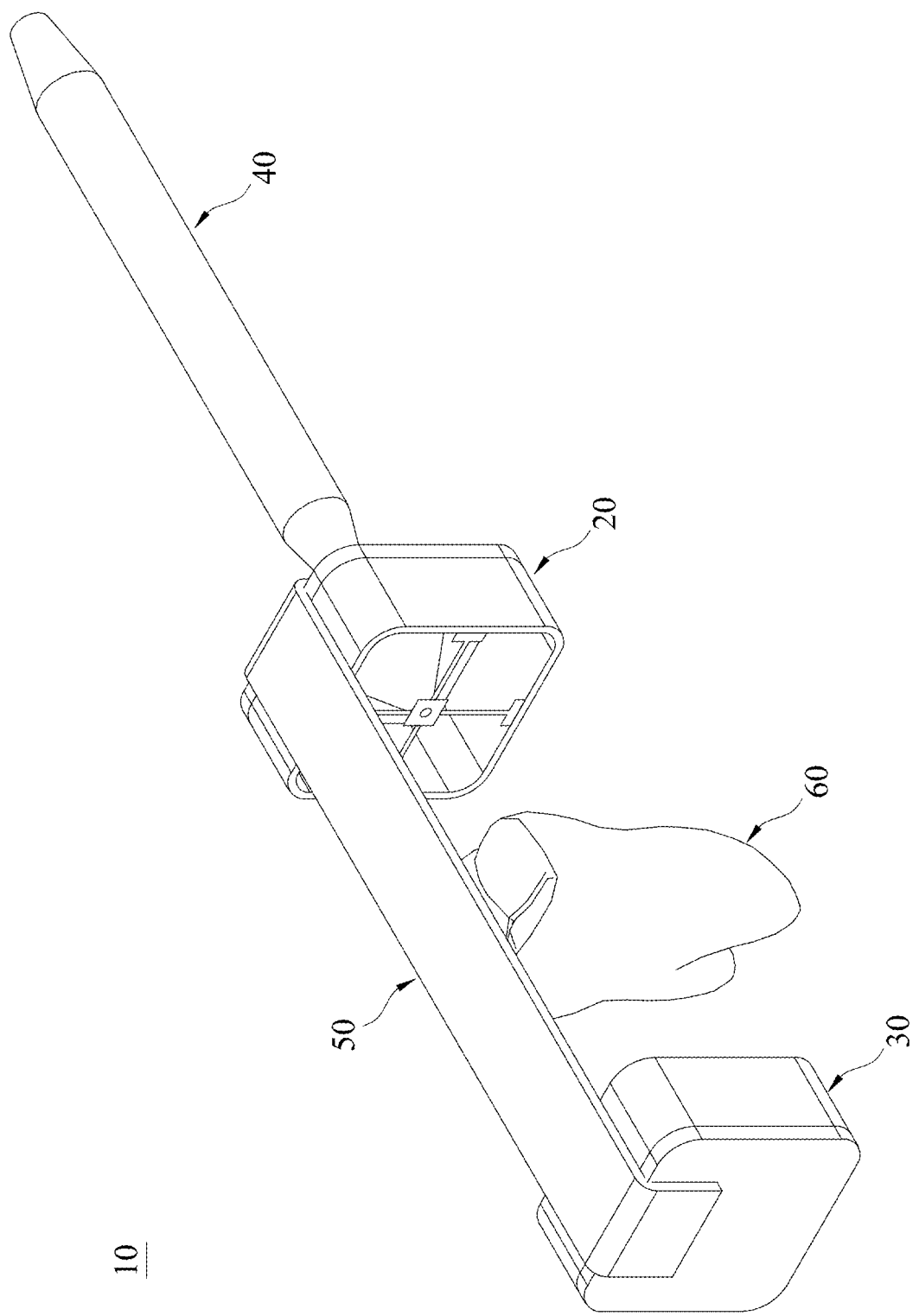
FIG. 1 is a schematic diagram of a device for reconstructing a real-time image of a target according to an embodiment of the present disclosure.

The following embodiments are used for illustrating the present disclosure. A person having ordinary skill in the art can easily conceive the other advantages and effects of the present disclosure, based on the disclosure of the specification. The present disclosure can also be implemented or applied as described in different examples. It is possible to modify or alter the examples for carrying out this disclosure without contravening its scope, for different aspects and applications.

The present subject matter will now be described with reference to the attached figures. Various structures, systems, and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

The proportional relationships, structures, sizes, and other features shown in accompanying drawings of this disclosure are only used to illustrate embodiments described herein, such that those with ordinary skill in the art can read and understand the present disclosure therefrom, of which are not intended to limit the scope of this disclosure. Any changes, modifications, or adjustments of said features, without affecting the designed purposes and effects of the present disclosure, should all fall within the scope of the technical content of this disclosure.

As used herein, the terms "comprise," "comprising," "include," "including," "have," "having," "contain," "containing," and any other variations thereof are intended to cover a non-exclusive inclusion. For example, when describing an object "comprises" a limitation, unless otherwise specified, it may additionally include other elements, components, structures, regions, parts, devices, systems, steps, or connections, etc., and should not exclude other limitations.

As used herein, sequential terms such as "first," "second," etc., are only cited in convenience of describing or distinguishing limitations such as elements, components, structures, regions, parts, devices, systems, etc. from one another, which are not intended to limit the scope of this disclosure, nor to limit spatial sequences between such limitations. Further, unless otherwise specified, wordings in singular forms such as "a," "an" and "the" also pertain to plural forms, and wordings such as "or" and "and/or" may be used interchangeably.

As used herein, the phrase "at least one," in reference to a list of one or more elements, should be understood to mean at least one element selected from any one or more of the elements in the list of elements, but not necessarily including at least one of each element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, the terms "one or more" and "at least one" may have the same meaning and include one, two, three, or more.

As used herein, the term "subject" may encompass any vertebrate including, but not limited to, humans, mammals, reptiles, amphibians, and/or fish. However, advantageously, the subject is a mammal such as a human, or an animal mammal such as a domesticated mammal, e.g., a dog, a cat, a horse, or the like, or a production mammal, e.g., a cow, a sheep, a pig, or the like. The term "patient" may be interchangeable with the "subject".

As used herein, the term "signal" refers to a radiation emitted from a source or reflected from an object, including but not limited to a beam, a terahertz beam, a signal, a terahertz signal. In at least one embodiment of the present disclosure, the signal may be penetrating and reflecting.

As used herein, the terms "distal end" and "proximal end" refer to the ends of a structure that are farther and closer from the THz source, respectively. For instance, as compared with the distal end of the taper structure, the proximal end of the taper structure is closer to the THz source disposed in the taper structure.

FIG. 1 illustrates an embodiment of the device 10 of the present disclosure that is configured for reconstruction arealtime image of a target 60 (e.g., a tooth). Specifically, the device 10 comprises a THz emitter 20, a receiver 30, and a generator 40. The aforesaid components can operate independently or respectively. Further, these components may be fully electronically controlled including the THz emitter 20, the receiver 30 and the generator 40 and in electrical communication with each other through wired or wireless. In some embodiments, the device 10 further comprises a connector 50 for detachable connecting the THz emitter 20 and the receiver 30 in a distance.

In at least one embodiment, the THz emitter 20 is configured for facing to the receiver 30, and the target 60 may be positioned between the THz emitter 20 and the receiver 30. As such, after the emission of terahertz signals from the THz emitter 20, the receiver 30 may collect the emitted terahertz signals passed through the target 60.

In at least one embodiment, the THz emitter 20 is connected to the generator 40 which may induce the THz emitter 20 to emit a terahertz signal, and the emitted terahertz signal may impact onto the surface of the target 60 and then reflect out. The reflected terahertz signal can be collected by the receiver 30, such that the device 10 may reconstruct the real-time image of the target 60.

In at least one embodiment, the connector 50 may adjust the distance between the THz emitter 20 and the receiver 30 to allow reconstructing the images of target 60 with different size. The detailed configuration of the emitter 20 and the receiver 30 will be further described hereinafter.

Figure 2:
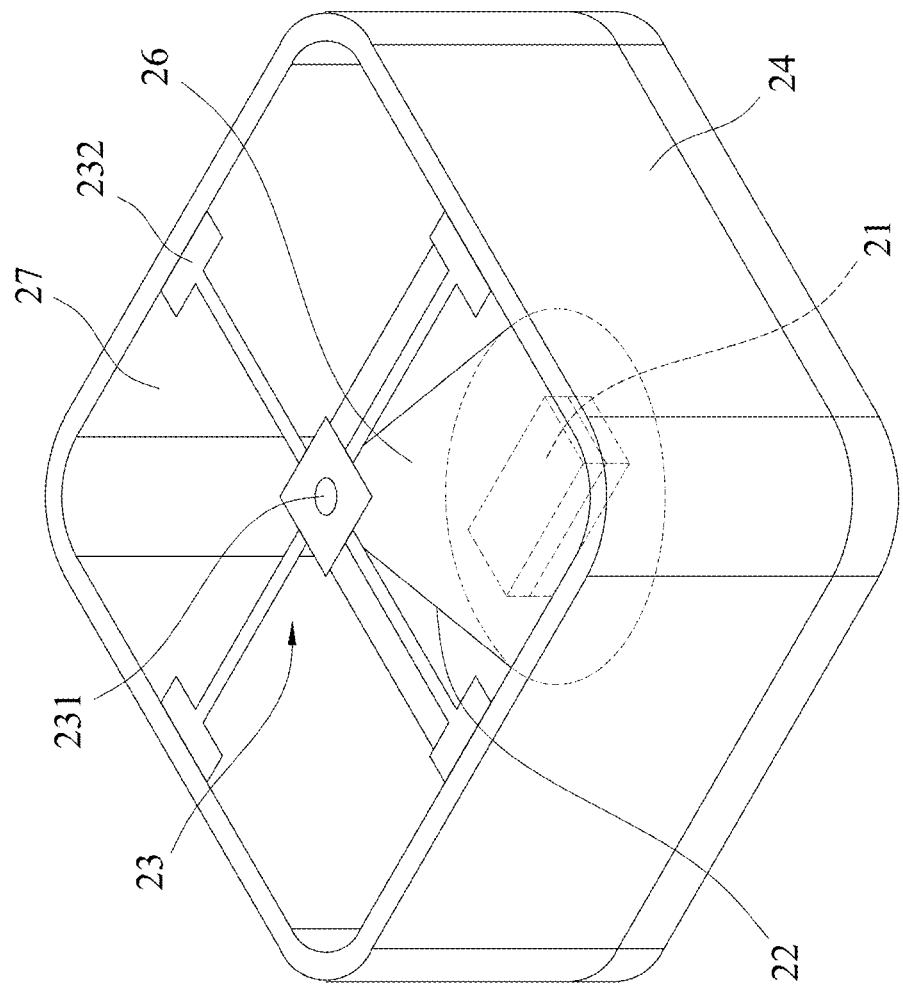
FIG. 2 is a schematic diagram of a THz emitter of the device for emitting a terahertz signal according to an embodiment of the present disclosure.

FIG. 2 shows an embodiment of the THz emitter 20 for emitting a terahertz signal of the present disclosure. The THz emitter 20 comprises a cover 24, a THz source 21 and a taper structure 22 integrated inside the cover, and a beam deflector module 23 arranged on atop surface 27 of the cover 24. In at least one embodiment, the THz source 21 is disposed on a bottom surface 26 inside the cover 24 of the THz emitter 20, and the taper structure 22 covering the THz source 21 is also disposed on the bottom surface 26 (as the THz source 721 and the taper structure 722 shown in FIG. 16). In some embodiments, the taper structure 22 may have a smaller aperture for emitting out the signal and a bigger aperture covering the THz source 21 to collect the signal. The detailed configuration of the THz source 21 will be further described hereinafter.

In at least one embodiment, the beam deflector module 23 may comprise a beam deflector 231 and one or more deflector electrodes 232. In some embodiments, the beam deflector 231 is positioned in the center of the top surface 27 of the cover 24 and electrically connected with the deflector electrode 232. In some other embodiments, the location of the beam deflector 231 may not be at the center of the top surface 27 of the cover 24 but at any location according to actual needs. In some embodiments, the deflector electrode 232 may extend outward from the beam deflector 231 to the edge of the top surface 27 of the cover 24.

In some embodiments, the shape of the cover 24 of the THz emitter 20 may be also fabricated as, but not limited to, a cubic, a cuboid, a cylinder, or other suitable shape according to actual needs.

Figure 3:
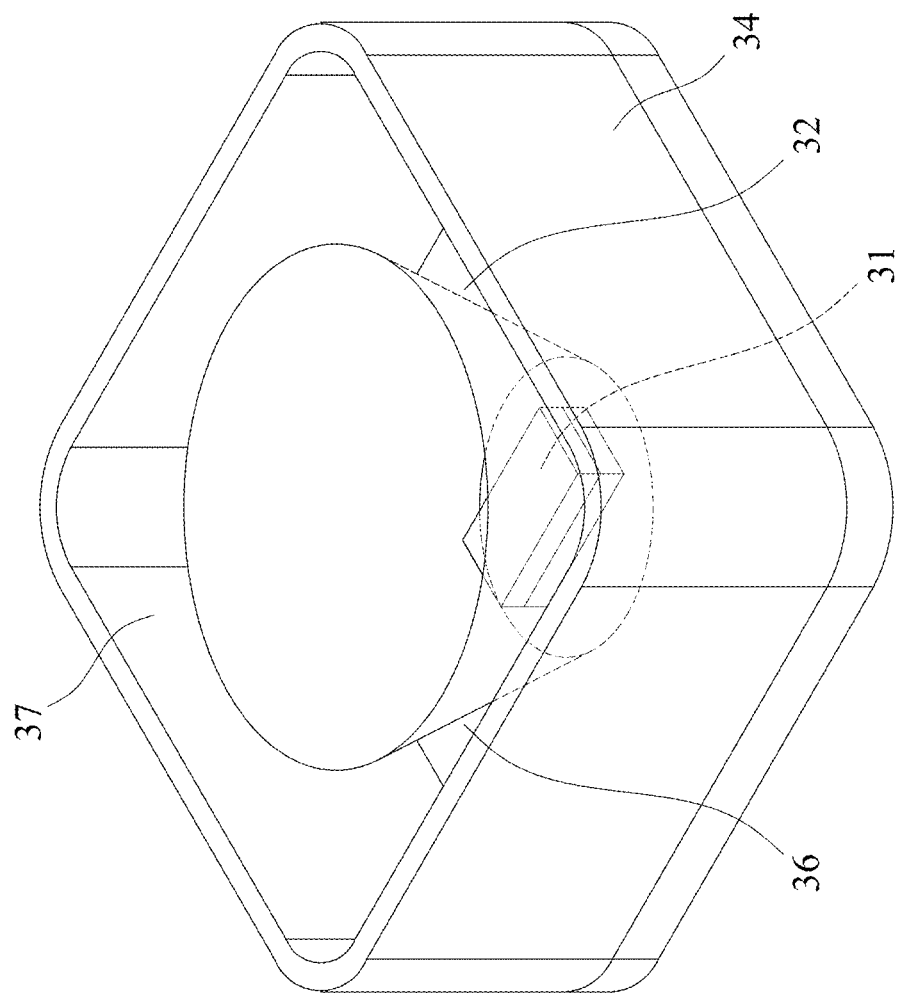
FIG. 3 is a schematic diagram of a receiver of the device for collecting a terahertz signal according to an embodiment of the present disclosure.

FIG. 3 shows an embodiment of the receiver 30 for collecting a terahertz signal of the present disclosure. The receiver 30 comprises a cover 34 similar with the cover 24 of the THz emitter 20, a THz detector 31, and a taper structure 32 similar with the taper structure 22 of the THz emitter 20. In at least one embodiment, the THz detector 31 is disposed on a bottom surface 36 inside the cover 34 of the receiver 30, and the taper structure 32 covering the THz detector 31 is also disposed on the bottom surface 36. In some embodiments, as comparing with the configuration between the THz source 21 and the taper structure 22 shown in FIG. 2, the configuration between the THz detector 31 and the taper structure 32 is upside down, i.e., the THz detector 31 is covered by the smaller aperture of the taper structure 32, and the bigger aperture of the taper structure 32 is directed to the top surface 37 of the cover 34 for collecting the terahertz signals.

Figure 4A:
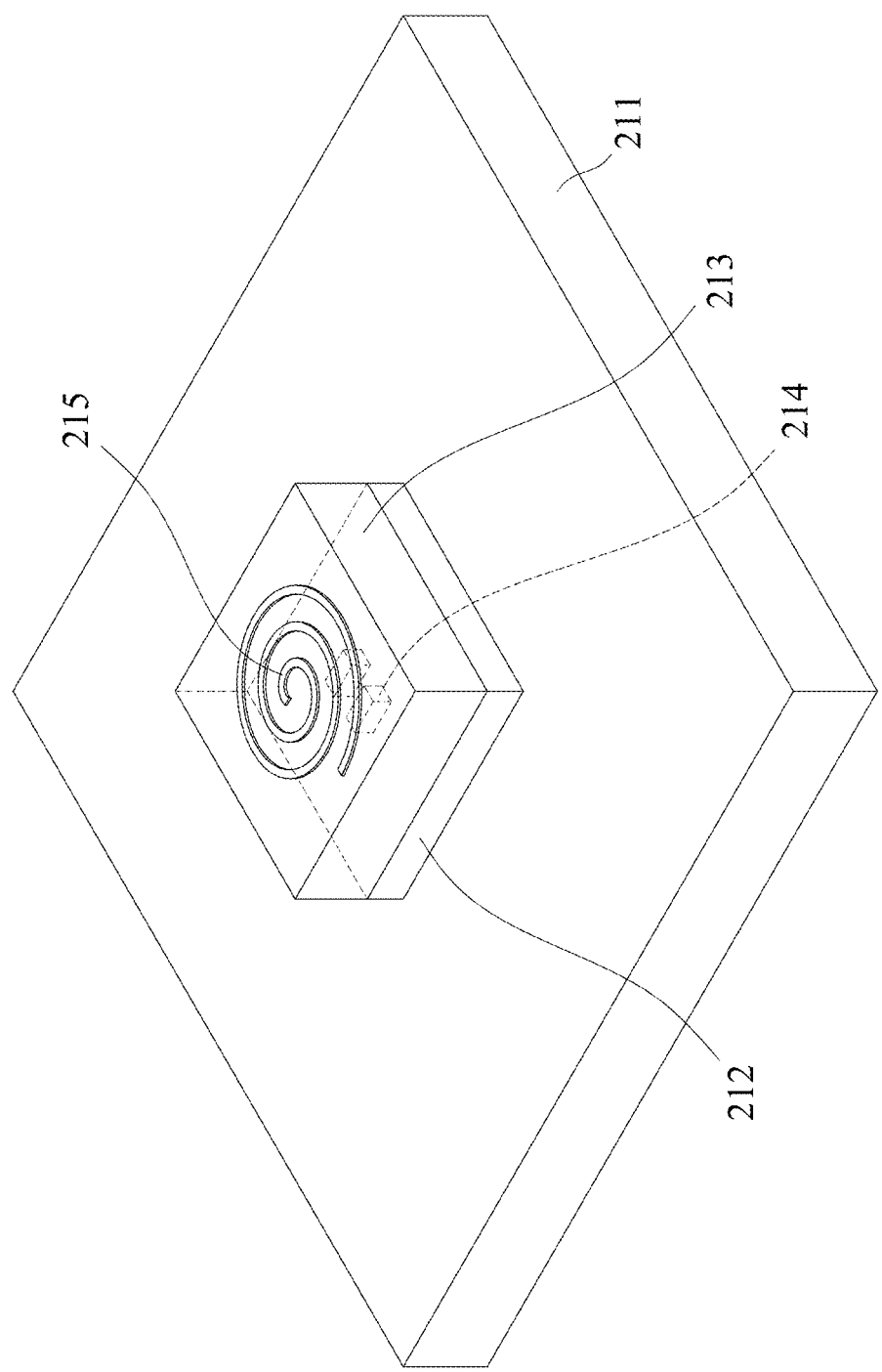
FIG. 4A is a schematic diagram of a THz source in the RTD (resonant tunneling diode) structure with an antenna according to an embodiment of the present disclosure.

Referring to FIG. 4A, it shows an embodiment of the THz source 21 of the present disclosure. The THz source 21 comprises a substrate 211, a RTD structure 212, a spacer layer 213, a resonator antenna 214 and a radiator antenna 215, and the spacer layer 213 acts as the separation between the resonator antenna 214 and the radiator antenna 215. For instance, the RTD structure 212 is disposed on the substrate 211; the spacer layer 213 is disposed on the RTD structure 212; the resonator antenna 214 is disposed on the RTD structure 212 and embedded in the spacer layer 213; and the radiator antenna 215 is disposed on the spacer layer 213. In some embodiments, the RTD structure 212 is disposed on the substrate by using conventional MBE (molecular beam epitaxy) and MOCVD (metal-organic chemical vapor deposition) depositions. In some embodiments, the substrate 211 is made of indium phosphide (InP), and the RTD structure 212 is fabricated as a structure of AlAs/InGaAs/AlAs.

Figure 4B:
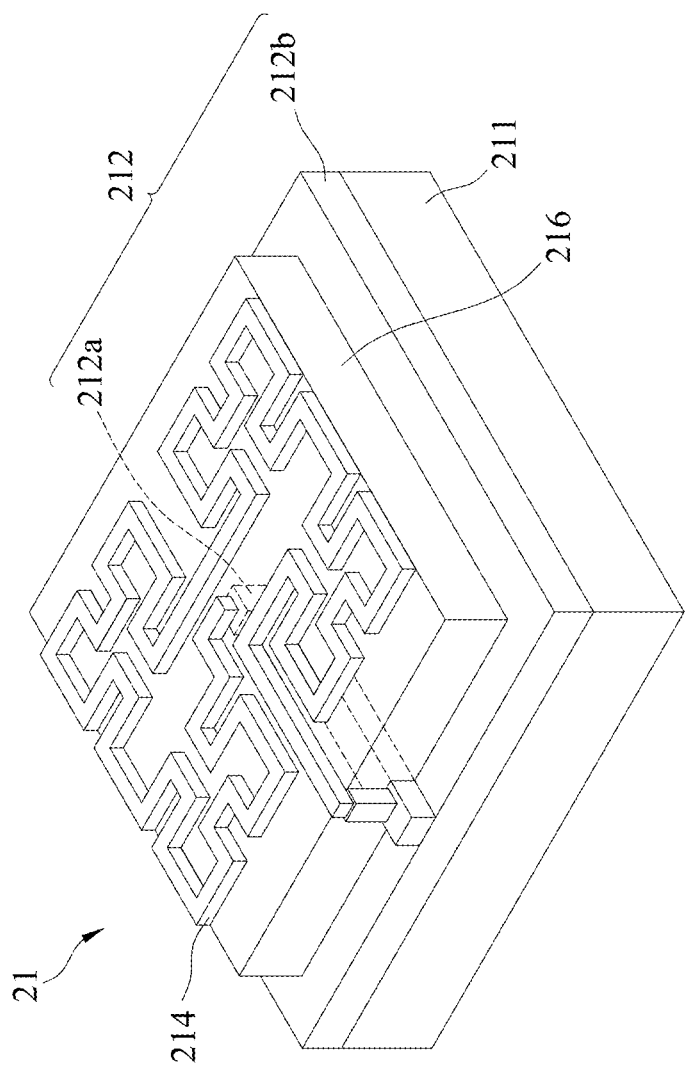
FIGS. 4B and 4C are schematic diagrams of a THz source in the RTD structure with an antenna according to the other embodiment of the present disclosure.
Figure 4C:
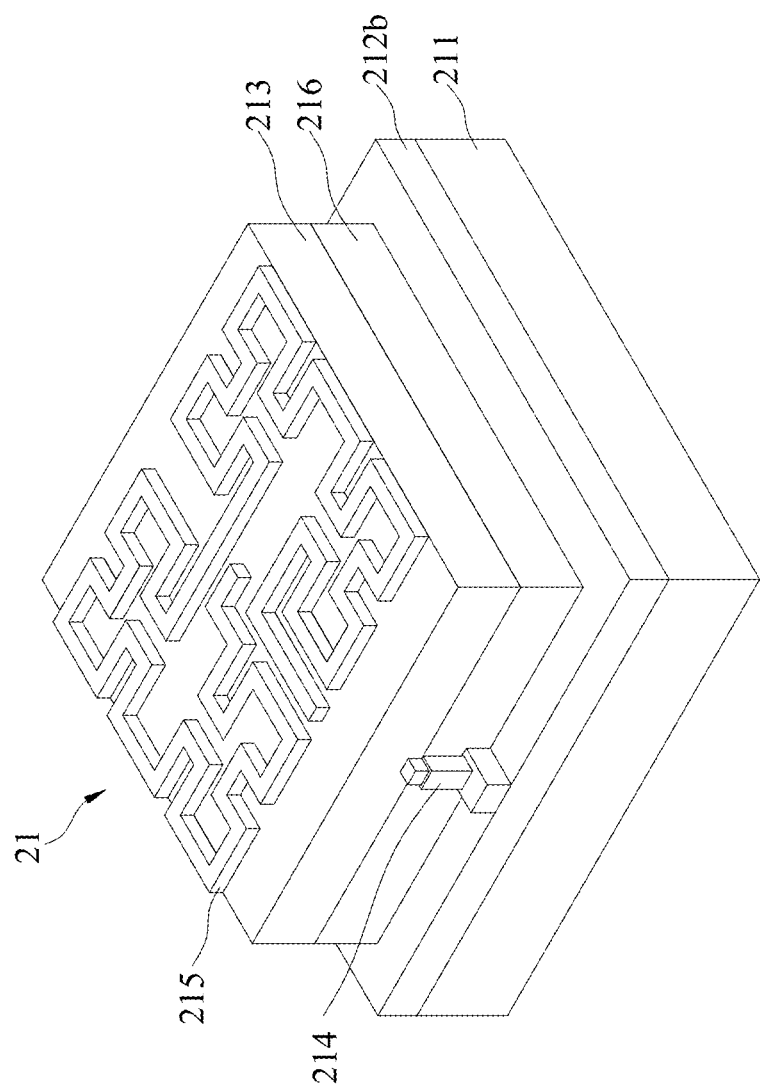

FIG. 4B and FIG. 4C show an embodiment of the THz source 21 of the present disclosure. The THz source 21 comprises a substrate 211, a RTD structure 212, a spacer layer 213, a resonator antenna 214, a passivation layer 216, and a radiator antenna 215, and the spacer layer 213 acts as the separation between the resonator antenna 214 and the radiator antenna 215. The radiator antenna 215 and the spacer layer 213 are removed in FIG. 4B to show the resonator antenna 214 more clearly. The RTD structure 212 comprises a RTD 212a disposed on a buffer layer 212b. In some embodiments, the buffer layer 212b may be made of $In_{0.53}Ga_{0.47}As$. In some embodiments, the RTD 212a may be a triple-barrier resonant tunneling diode (TBRTD). In some embodiments, the passivation layer 216 may be made of silicon dioxide. In some embodiments, the buffer layer 212b is disposed on the substrate 211; the passivation layer 216 is disposed on the buffer layer 212b; the RTD 212a is embedded in the passivation layer 216; the main section of the resonator antenna 214 is disposed on the passivation layer 216. In some embodiments, a top electrode of the resonator antenna 214 is electrically connected to an emitter end of the RTD 212a, while a bottom electrode of the resonator antenna 214 is electrically connected to a collector end of the RTD 212a. In some embodiments, the top electrode of the resonator antenna 214 is embedded in the passivation layer 216, while the bottom electrode of the resonator antenna 214 is disposed on the buffer layer 212b and is embedded in or covered by the passivation layer 216. In some embodiments, the spacer layer 213 is disposed on the passivation layer 216 and the resonator antenna 214, and the radiator antenna 215 is disposed on the spacer layer 213.

In at least one embodiment, the resonator antenna 214 and/or the radiator antenna 215 may be a spiral antenna structure or any broadband antenna or tunable antenna. In some embodiments, the resonator antenna 214 and the radiator antenna 215 are fractal antennas shaped according to the same fractal curve or fractal pattern. Therefore, the radiator antenna 215 has the same shape and the same size as those of the main section of the resonator antenna 214. In addition, the radiator antenna 215 and the main section of the resonator antenna 214 are aligned vertically. For example, the resonator antenna 214 and the radiator antenna 215 shown in FIG. 4B and FIG. 4C are both shaped according to the Hilbert curve. In some embodiments, the resonator antenna 214 and the radiator antenna 215 may be shaped according to another fractal curve or fractal pattern, such as the Koch curve, the Peano curve, the Sierpinski gasket, or the Minkowski geometry.

Figure 4D:
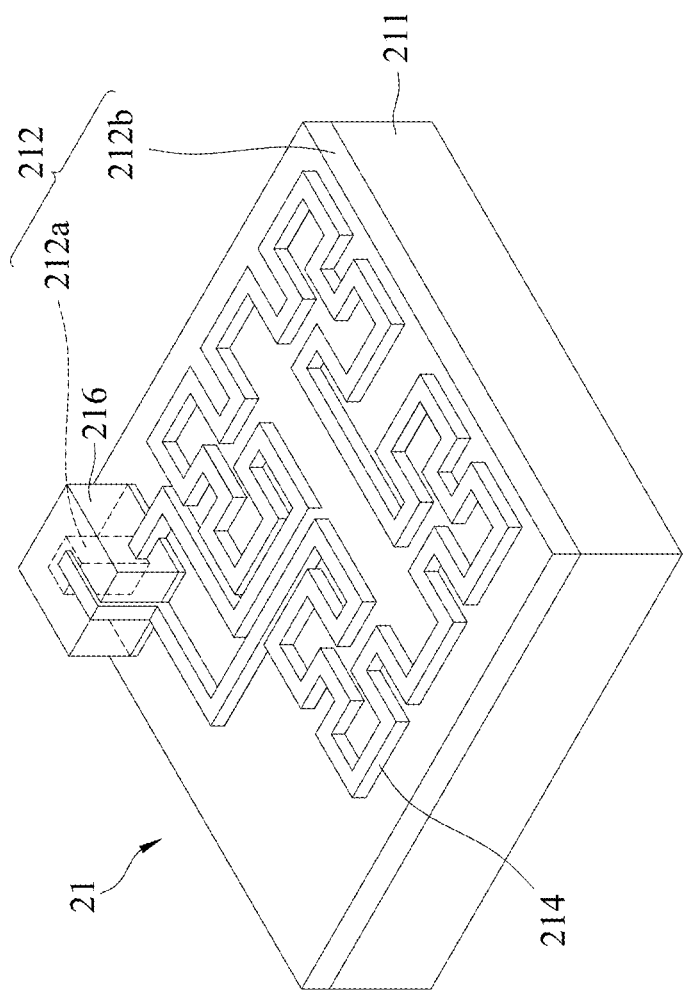
FIG. 4D is a schematic diagram of a THz source in the RTD structure with an antenna according to another embodiment of the present disclosure.

Referring to FIG. 4D, it shows an embodiment of the THz source 21 of the present disclosure, which is an alternate design as compared with that in FIGS. 4B and 4C. The main section of the resonator antenna 214 of the THz source 21 is fabricated on the substrate 211 or the buffer layer 212b. In FIG. 4D, the spacer layer 213 and the radiator antenna 215 are removed and only a small part of the passivation layer 216 is shown, so as to show the RTD 212a and the resonator antenna 214 more clearly. In fact, the passivation layer 216 of the THz source 21 may have approximately the same size as its counterpart in FIG. 4B, such that the passivation layer 216 covers the resonator antenna 214. Also, the THz source 21 comprises a spacer layer 213 disposed on the passivation layer 216 and a radiator antenna 215 fabricated on the spacer layer 213. The resonant tunneling diodes are suitable for terahertz source 21 and detector 31 in the portable device 10 of the present disclosure due to their simple design, conventional semiconductor fabrication methods and integration advantages over other terahertz sources. The resonant tunneling diodes can perform both terahertz emission and detection when they biased in different regions. The RTD structure 212 emit the terahertz radiation when they biased in the negative differential region (NDR), and they can detect the terahertz radiation if operated in the non-linearity region of their voltage-current response.

In some embodiments, the RTD structure 212 of the THz source 21 may be configured to emit and sense the terahertz radiation ranging between 0.4 THz to 0.5 THz. The dental tissues can exhibit better imaging contrast at this terahertz range, and the atmospheric water absorption is low at 0.4 THz to 0.5 THz as compared with the other range of terahertz spectrum. As such, the proposed portable THz scanners are able to perform dental imaging in situ or in vivo even in the high humid atmosphere such as the human mouth.

In at least one embodiment, RTD structures are fabricated with a slot resonator antenna (as shown in FIG. 4A) or the other antenna structure (as shown in FIG. 4B) to couple the generated terahertz radiation to the free space through the silicon lens mounted at the backside of the substrate. Hemispherical or hyper-hemispherical silicon lenses are used in such configurations, but those silicon lenses are expensive and impose difficulty in packaging. Therefore, in some embodiments, the radiator antenna 215 is arranged on the spacer layer 213

Using a square patch antenna on the top of the dielectric covering the slot resonator antenna 214 of the RTD structure 212 can inductively couple the generated terahertz oscillation to the patch antenna and can emit the radiation in the upward direction and thus eliminates the use of silicon lens in the THz source. However, the achieved efficiency is only about 25% at 510 GHz due to the structural limitation of the square patch antenna used.

Therefore, in some embodiments, the radiator antenna 215 may be formed as a spiral-antenna structure (as shown in FIG. 4A) or similar kind of broadband antenna structure (as shown in FIG. 4B) on the top of the spacer layer 213 of the THz source 21 to emit (or receive) the terahertz signal without using the silicon lens. The free-space coupling (or receiving) efficiency of the antenna structure on the top of the spacer layer can be enhanced by carefully designing the antenna geometry and optimizing the dielectric thickness, of which the present disclosure is not limited thereto.

Figure 5:
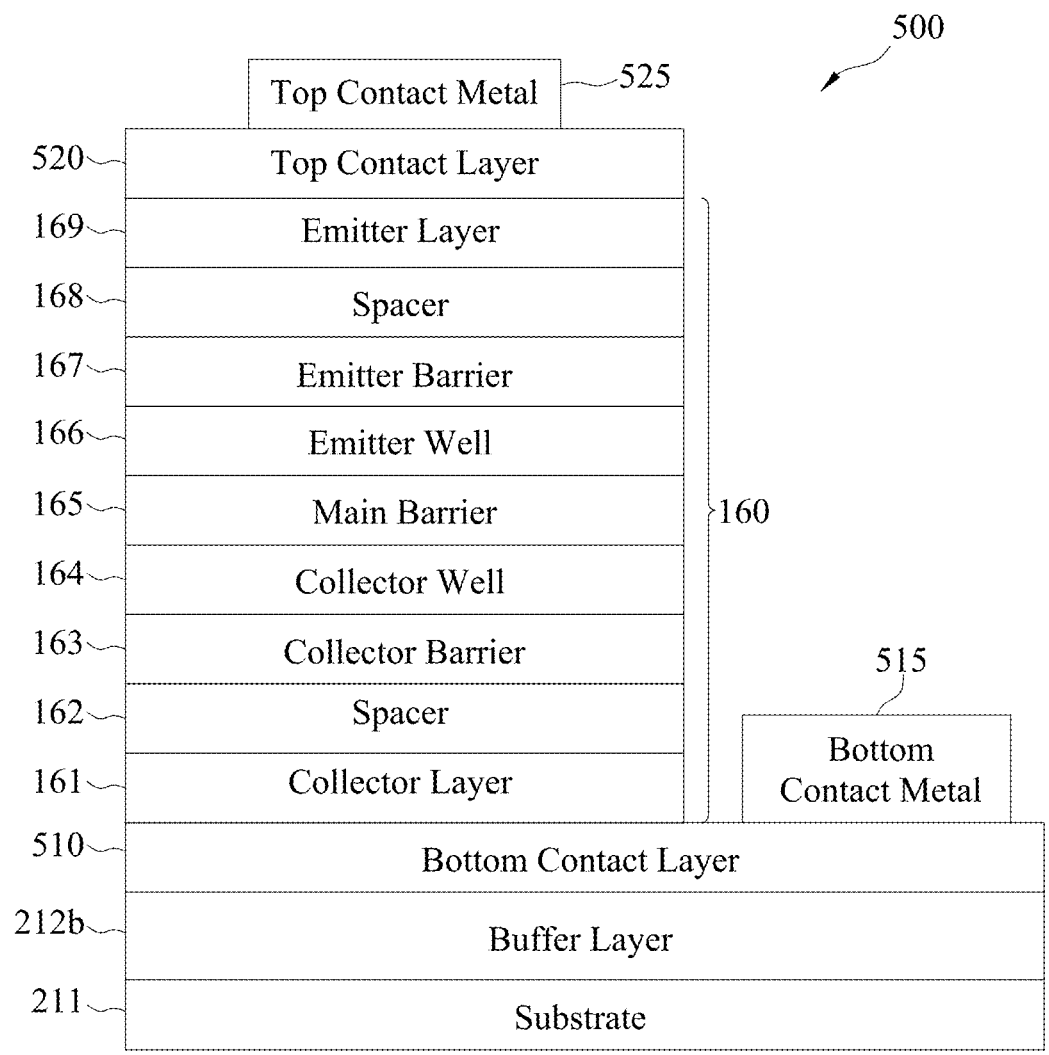
FIG. 5 is a cross-sectional view of a part of a THz source according to an embodiment of the present disclosure.

FIG. 5 is a cross-sectional view of a part of a THz source 500 according to an embodiment of the present disclosure. The THz source 500 includes all of the components and the layers of the THz source 21 shown in FIG. 4B and FIG. 4C. In addition, the THz source 500 further includes a bottom contact layer 510 disposed between the buffer layer 212b and the TBRTD 160, a top contact layer 520 formed on TBRTD 160, a bottom contact metal 515 formed on the bottom contact layer 510, and a top contact metal 525 formed on the top contact layer 520. The bottom contact metal 515 and the top contact metal 525 may be formed by sputtering gold and be terminal parts of the resonator antenna 214.

As shown in FIG. 5, the TBRTD 160 includes 9 stacked layers, which are, from bottom to top, a collector layer 161, a spacer 162, a collector barrier 163, a quantum well (collector well) 164, a main barrier 165, another quantum well (emitter well) 166, an emitter barrier 167, a spacer 168, and an emitter layer 169. The following Table 1 lists the material, thickness and molar concentration of silicon doping of each layer from the top contact layer 520 to the buffer layer 212b in FIG. 5.

TABLE 1

| Numeral | Layer | Material | Thickness (nm) | Doping (cm$^{-3}$) |
| --- | --- | --- | --- | --- |
| 520 | top contact layer | $In_{0.53}Ga_{0.47}As$ | 50 | $3 \times 10^{19}$ |
| 169 | emitter layer | $In_{0.53}Ga_{0.47}As$ | 50 | $2 \times 10^{18}$ |
| 168 | spacer | $In_{0.53}Ga_{0.47}As$ | 5 | 0 |
| 167 | emitter barrier | AlAs | 1.2 | 0 |
| 166 | emitter well | $In_{0.53}Ga_{0.47}As$ | 6.5 | 0 |
| 165 | main barrier | $In_{0.52}Al_{0.48}As$ | 2.4 | 0 |
| 164 | collector well | $In_{0.53}Ga_{0.47}As$ | 4.5 | 0 |

TABLE 1-continued

| Numeral | Layer | Material | Thickness (nm) | Doping (cm$^{-3}$) |
|---|---|---|---|---|
| 163 | collector barrier | AlAs | 1.2 | 0 |
| 162 | spacer | In$_{0.53}$Ga$_{0.47}$As | 5 | 0 |
| 161 | collector layer | In$_{0.53}$Ga$_{0.47}$As | 50 | $2 \times 10^{18}$ |
| 510 | bottom contact layer | In$_{0.53}$Ga$_{0.47}$As | 400 | $3 \times 10^{19}$ |
| 212b | buffer layer | In$_{0.53}$Ga$_{0.47}$As | 3000 | $1 \times 10^{16}$ |

In a traditional double-barrier RTD or DBRTD, the emitter and collector barriers are identical (identical barrier material and thickness), and the device structure is symmetrical to avoid quick thermal leakage current and to increase the tunneling current.

By contrast, the triple barriers of the TBRTD 160 provided by the present disclosure includes more quantum wells and barriers, which increases well charge and peak current, and lowers peak voltage. Moreover, the TBRTD 160 includes a non-identical main barrier 165. As listed in Table 1, while the collector barrier 163 and the emitter barrier 167 have identical material and thickness, the main barrier 165 is formed by the different material and has different thickness. Further, the collector well 164 and the emitter well 166 are also asymmetrical because of their different thicknesses. Therefore, the aforementioned asymmetrical structure enhances the tunneling current and increases the maximum operating frequency limit.

As shown in Table 1, the main barrier 165 is made of In$_{0.52}$Al$_{0.48}$As. The collector barrier 163 and the emitter barrier 167 are made of AlAs. The other layers listed in Table 1 are all made of In$_{0.53}$Ga$_{0.47}$As. The TBRTD 160 adopts the InGaAs/InAlAs/AlAs material combination because this material system offers better RTD properties. The spacers 162 and 168 are undoped —In$_{0.53}$Ga$_{0.47}$As to avoid the diffusion of charge carriers from the highly doped layers.

The TBRTD 160 shows a simulated peak current density of 440 kA/cm$^2$ and a DC-RF conversion efficiency up to 19.75%. Theoretically calculated maximum extractable output power of the TBRTD 160 is about 250 μW at 0.95 THz for a device area of 1 μm$^2$, which is much higher than the previously reported output power of a traditional TBRTD. The non-identical triple barrier structure of the TBRTD 160 exhibits ΔV of 0.41 V and ΔI of 0.0033 A, wherein ΔV and ΔI are respectively the voltage and the current of the negative differential resistance (NDR) region of the TBRTD 160. The peak-to-valley current ratio (PVCR) is about 4.71. Compared to a traditional TBRTD, the peak current and the peak voltage of the TBRTD 160 are lowered without compromising the PVCR, which simultaneously increases the DC-RF conversion efficiency as well. The maximum oscillation frequency of the TBRTD 160 is 0.95 THz. The theoretically estimated parasitic capacitance of the TBRTD 160 is $c_n$=21.3 fF. The series resistance of the TBRTD 160 is $R_s$=3.25Ω. The reciprocal of the negative conductance of the TBRTD 160 is $R_n$=18.66Ω.

Figure 6:
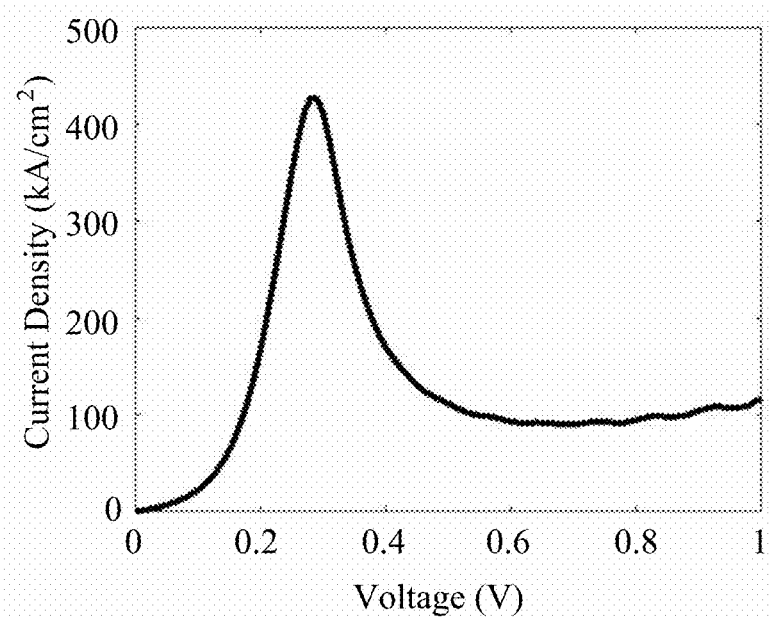
FIG. 6 is an exemplary graph showing the voltage versus current density characteristic of a triple barrier RTD (TBRTD) according to an embodiment of the present disclosure.

FIG. 6 is an exemplary graph showing the numerically simulated voltage versus current density characteristic of the TBRTD 160 with a device area of 1 μm$^2$.

Figure 7:
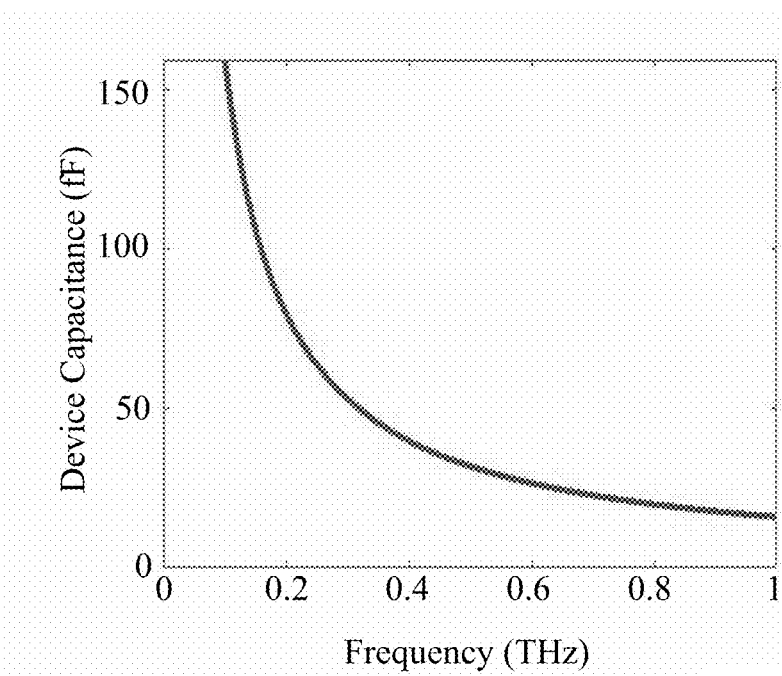
FIG. 7 is an exemplary graph showing the estimated device capacitance versus maximum oscillation frequency characteristic of a TBRTD according to an embodiment of the present disclosure.

FIG. 7 is an exemplary graph showing the estimated device capacitance versus maximum oscillation frequency characteristic of the TBRTD 160 with a device area of 1 μm$^2$.

In some embodiments, the resonator antenna 214 and the radiator antenna 215 of the THz source 500 may be fractal antennas because fractal technology allows miniature antennas and integration of multiple bands. The fractal antennas have desirable properties such as space filling, self-similarity, fractional dimensions, infinite complexity, mechanical simplicity, and robustness, which make fractal antennas unique to attain advantages like miniaturization, wideband, and multiband characteristics with better efficiency. The space filling property is used to reduce antenna size. The self-similarity is used to achieve multiband resonator antenna. The number of iterations of the geometries of the resonator antenna 214 and the radiator antenna 215 are based on their operating wavelengths.

Further, the radiator antenna 215 of the THz source 500 may be a reconfigurable fractal antenna so as to expand its operational frequency range. The radiator antenna 215 can be adjusted to achieve either re-configurability or tunability in the desired frequency range for wireless communications.

Figure 8:
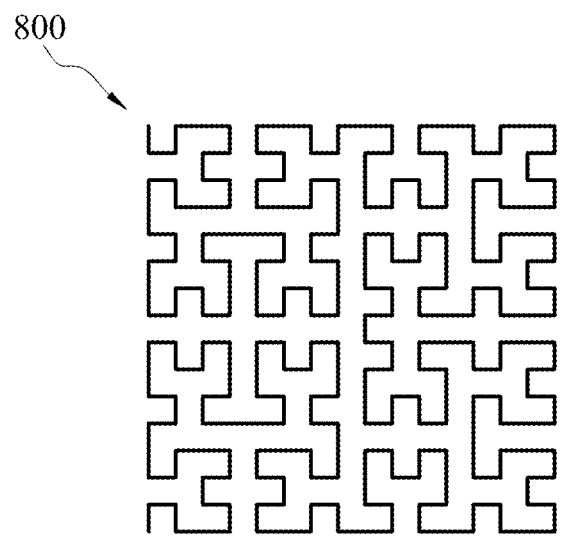
FIGS. 8-11 are schematic diagrams showing frequency-tunable fractal antennas of THz sources according to different embodiments of the present disclosure.
Figure 9:
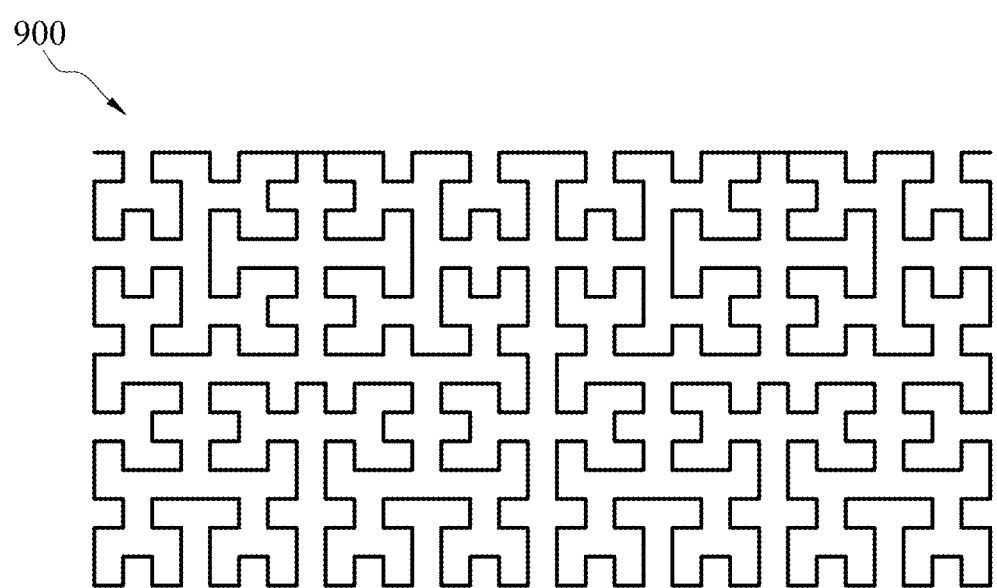
Figure 12:
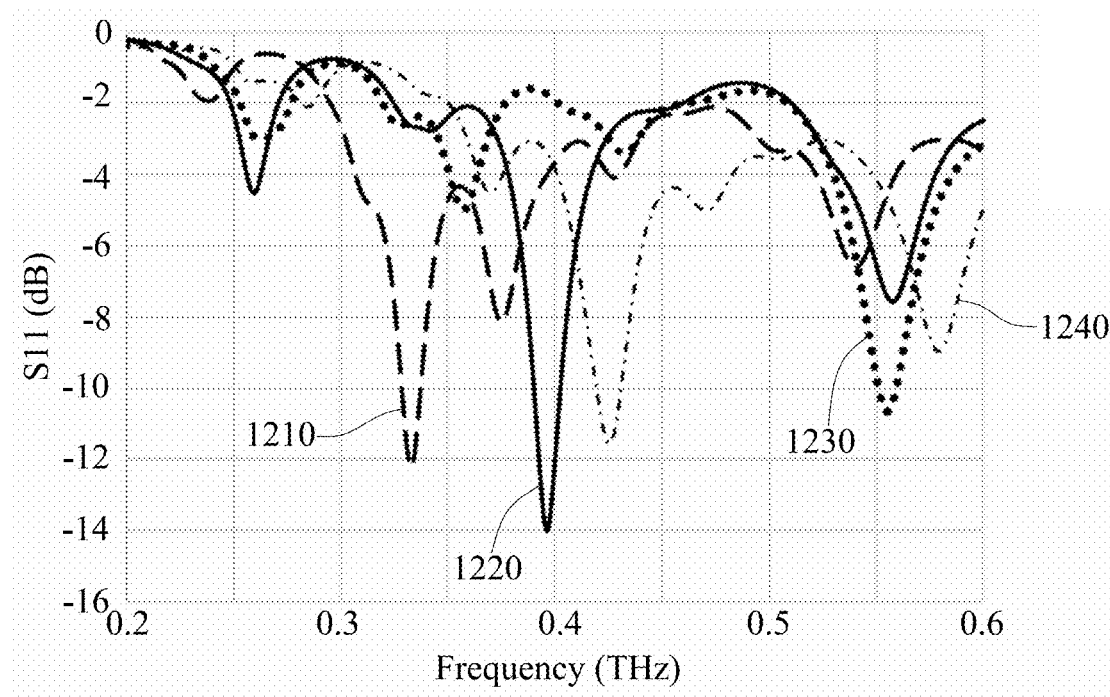
FIGS. 12 and 13 are exemplary graphs showing frequency shifts of frequency-tunable fractal antennas of THz sources according to different embodiments of the present disclosure.

In some embodiments, for a large frequency shift, a large section of electrical length or a large segment of fractal patterns can be simply disconnected from the radiator antenna 215, hence reducing the overall size of the radiator antenna 215 and generating an upward frequency shift. On the other hand, more electrical length or more fractal patterns can be connected to the radiator antenna 215, hence increasing the overall size of the radiator antenna 215 and generating a downward frequency shift. The radiator antenna 215 may include at least one switch embedded in the fractal curve or the fractal pattern of the radiator antenna 215. The at least one switch may be implemented by the diode or transistor for connecting and disconnecting one or more sections or segments of the radiator antenna 215 to reconfigure the radiator antenna 215 for frequency shifts. For example, in an embodiment, the radiator antenna 215 may be switched between the one-segment fractal curve 800 shown in FIG. 8 and the two-segment fractal curve 900 shown in FIG. 9. When the radiator antenna 215 is switched to the one-segment fractal curve 800 in FIG. 8, its reflection coefficient S11 is plotted as the curve 1210 shown in FIG. 12. When the radiator antenna 215 is switched to the two-segment fractal curve 900 in FIG. 9, its reflection coefficient S11 is plotted as the curve 1220 shown in FIG. 12.

Figure 10:
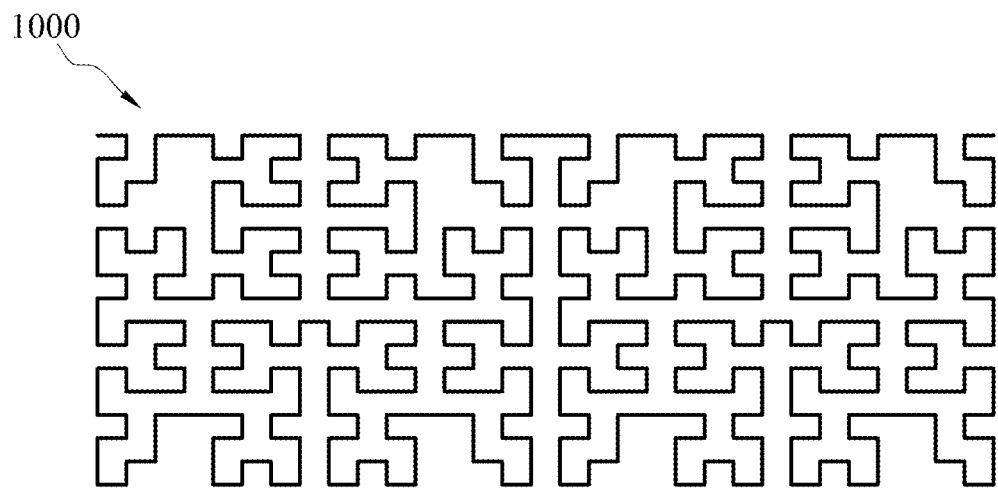
Figure 11:
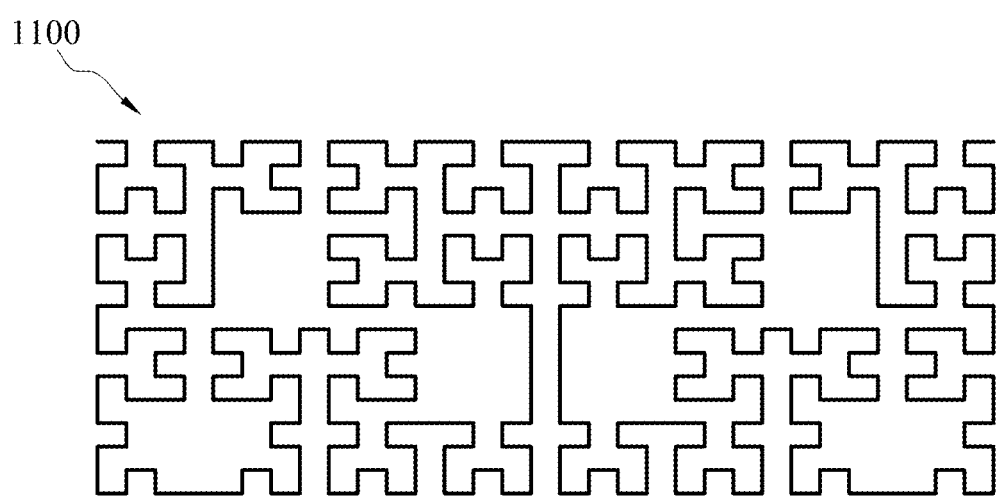

In some embodiments, for a medium frequency shift, fewer fractal patterns or less electrical length can be disconnected from or connected to the radiator antenna 215 by controlling the switches embedded in the radiator antenna 215. The effect can either decrease the electrical length of the radiator antenna 215, which increases the operating frequency, or vice versa. For example, in an embodiment, the radiator antenna 215 may be further switched between the fractal curve 1000 shown in FIG. 10 and the fractal curve 1100 shown in FIG. 11. When the radiator antenna 215 is switched from the fractal curve 900 in FIG. 9 to the fractal curve 1000 in FIG. 10, three arms are cut from each fractal segment, which increases electrical length. The resultant reflection coefficient S11 is plotted as the curve 1230 shown in FIG. 12. An approximately 0.02 THz downward (leftward) frequency shift is observed. When the radiator antenna 215 is switched to the fractal curve 1100 in FIG. 11 with larger cut and electrical length reduction, the reflection coefficient S11 is plotted as the curve 1240 shown in FIG. 12. Here, upward (rightward) frequency shift is observed.

In some embodiments, similar to the radiator antenna 215, the resonator antenna 214 may include at least one switch implemented by diode or transistor for connecting and disconnecting one or more sections, segments, or arms of the resonator antenna 214 to reconfigure the resonator antenna 214 for large and medium frequency shifts.

In some embodiments, both of the resonator antenna 214 and the radiator antenna 215 include switches for large and medium frequency shifts.

In some embodiments, for a fine frequency shift or continuous frequency tuning, the spacer layer 213 underneath the radiator antenna 215 may include a ferroelectric material, such as polymer dispersed liquid crystal (PDLC), whose permittivity changes when the electric field applied to the ferroelectric material changes. Different from the aforementioned reconfiguration of the fractal pattern where the frequency shift is more discrete and highly dependent on the fractal pattern, the voltage induced dielectric constant change in the radiator antenna 215 can create much more continuous and infinitesimal change of the operating frequency.

Figure 13:
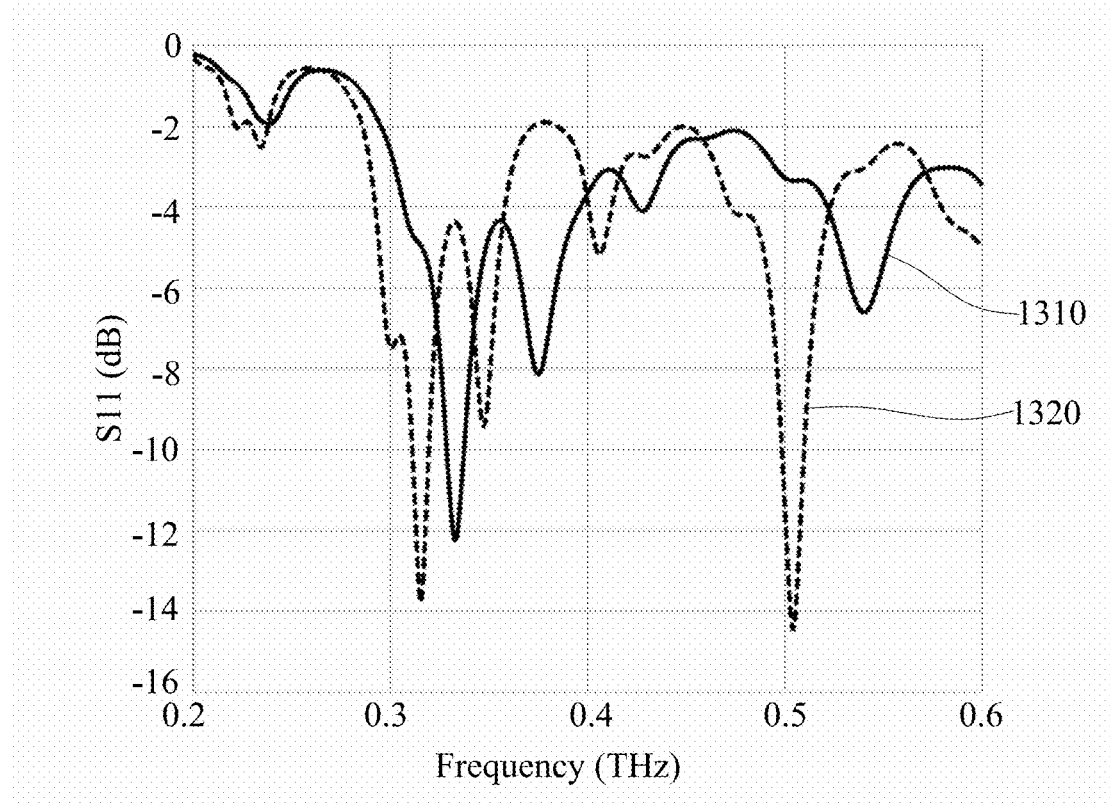

An example of this frequency shift due to permittivity change using a spacer layer 213 consisting of PDLC on the radiator antenna 215 is shown in FIG. 13, wherein frequency shifts are due to the liquid crystals in the spacer layer 213 changing from an ordinary polarization state (corresponding to the curve 1310) to an extraordinary polarization state (corresponding to the curve 1320). The operating frequency of the radiator antenna 215 changes proportionally with the permittivity of the PDLC in the spacer layer 213.

In some embodiments, the substrate 211, the buffer layer 212b, or the passivation layer 216 underneath the resonator antenna 214 may include a ferroelectric material such as PDLC for a fine frequency shift or continuous frequency tuning of the resonator antenna 214.

In some embodiments, the substrate 211, the buffer layer 212b or the passivation layer 216 underneath the resonator antenna 214 and the spacer layer 213 underneath the radiator antenna 215 may both include ferroelectric materials such as PDLC for fine frequency shifts or continuous frequency tuning of the resonator antenna 214 and the radiator antenna 215.

Figure 14:
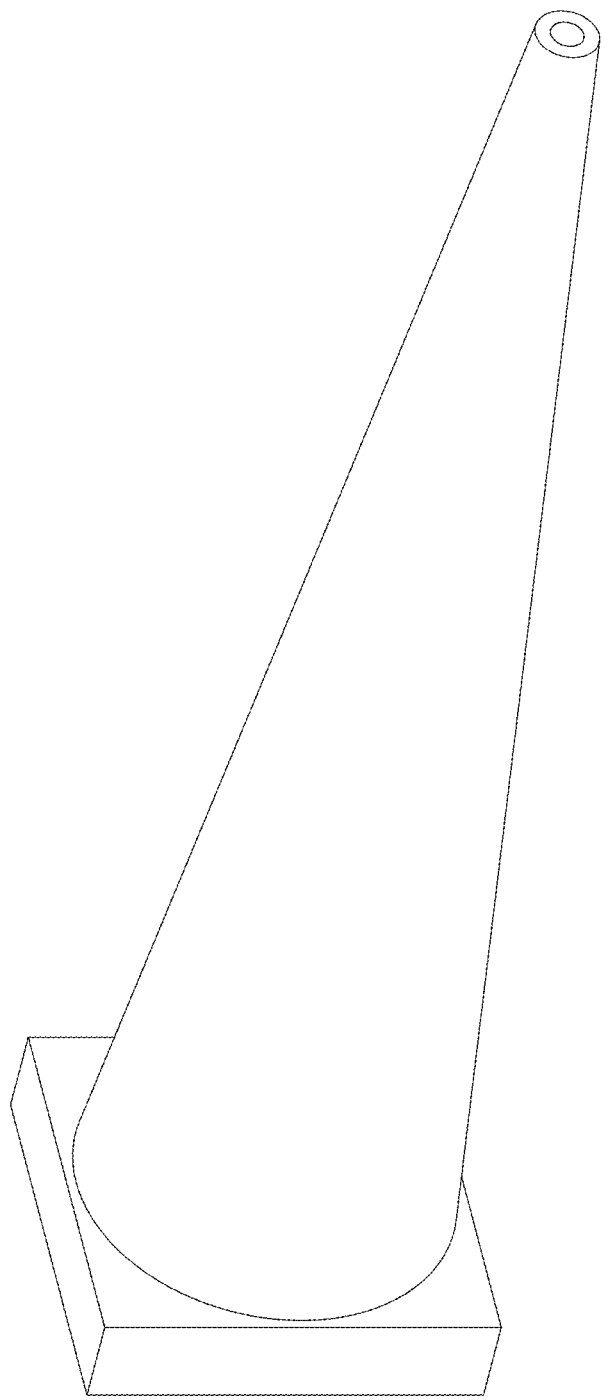
FIG. 14 is a schematic diagram of a taper structure of a THz source according to an embodiment of the present disclosure.

FIG. 14 shows an embodiment of a taper structure 22 or 32 of the THz source of the present disclosure. The taper structure 22 of the THz emitter 20 and the taper structure 32 of the receiver 30 are a hollow-polymer taper structure having an entry aperture at the proximal end and an emitting aperture at the distal end, and the entry aperture is larger than the emitting aperture. For instance, the taper structure 22 is covering the THz source 21 by the entry aperture side of the taper structure 22, whereas the taper structure 32 is covering the THz detector 31 by the emitting aperture side of the taper structure 32. In some embodiments, the taper structure 22 or 23 of the THz source is a tapered waveguide structure.

The electrical filed at the tapered-tip (i.e., emitting aperture of the taper structure) is strongly influenced by the probe design. There may increase the electric field strength by several ways such as increased source power, lowering the transmission losses, improved impendence matching, and large aperture diameter and shorter probe length. However, increasing the THz source power and improving impendence matching may increase the cost and complexity of the imaging system. Also, the bigger the diameter of the aperture may cause the lower the image resolution. Accordingly, in some embodiments, decreasing the transmission losses of terahertz waves within the waveguide and the probe structure is a suitable way to achieve the strong electric field localization at the tapered-tip.

To decrease the transmission losses of terahertz signals, it is better to choose a proper material that forms the taper structure. Terahertz transmission loss is related to the imaginary part of dielectric constant ($\epsilon = \epsilon' + j \epsilon''$, where E is the dielectric constant, $\epsilon'$ and $\epsilon''$ are the real and imaginary parts of the dielectric constant, respectively). By using a taper structure coated with a metal, the imaginary part of the dielectric constant is absence at the air-core of the taper structure (hollow part of the taper structure). Due to the waveguide nature of the tip, the absence of the imaginary part of the dielectric constant in the hollow taper structure is beneficial to have high electric field strength at the nearfield distance of the tapered-tip. The nearfield distance is defined as $$< \frac{2D^2}{\lambda},$$

where D is the aperture diameter of the taper structure, and $\lambda$ is the wavelength of the terahertz signal.

Figure 15A:
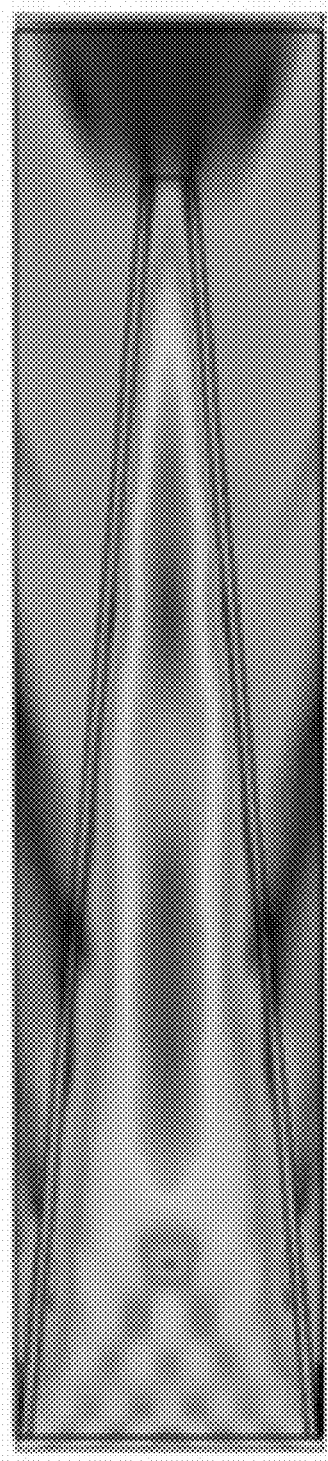
FIG. 15A is a simulated electric field response of the hollow-polymer taper structure without metal coating.
Figure 15B:
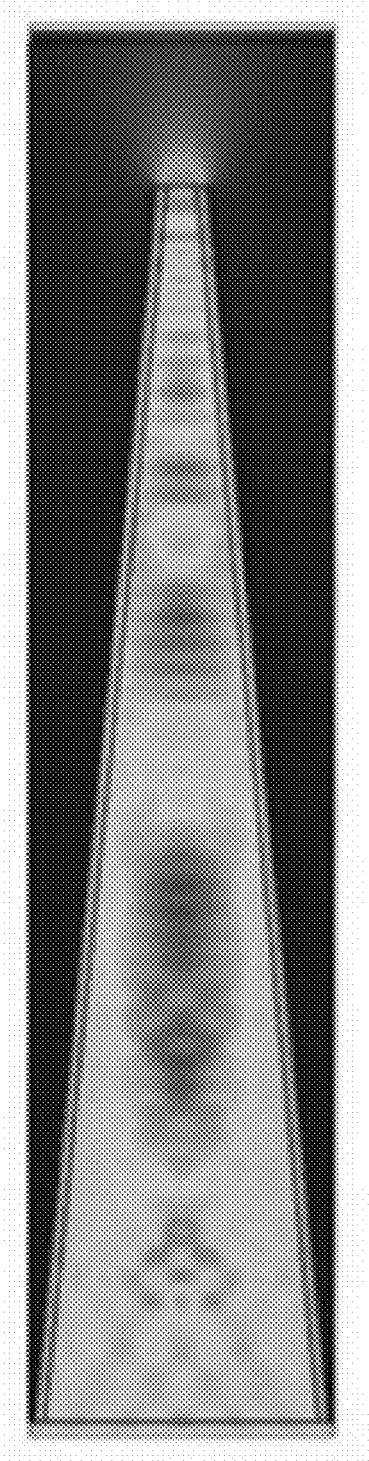
FIG. 15B is a simulated electric field response of the hollow-polymer taper structure with inner wall metal coating.

FIGS. 15A and 15B shows the simulated electric field response of the hollow-polymer taper structure with and without metal coating, respectively. The cross-section electric field profile of the hollow-HDPE (High-Density Polyethylene) taper structure 61 is shown in FIG. 15A. It shows that the localized electric field at the tapered-tip (i.e., emitting aperture) of the hollow-HDPE taper structure 61 is not significant owing to the resonance of the input THz signal occurred at the air-core and the leakage wave observed outside the hollow-taper without metal coating due to the mismatch of the waveguide condition at the air-core and inner HDPE interface.

In some embodiments, the air-core part of the taper structure of the present disclosure has an inner wall coated with a metal to form a metal-coated hollow-polymer taper and to help guide and generate focused near field beam profile at the exit of the taper end. This nearfield operation allows the spatial image resolution to go beyond diffraction limit and further enhance the overall image resolution. Referring to FIG. 15B, it shows a simulated electric field response of a metal-coated hollow-polymer taper of the present disclosure. The metal-coated hollow-polymer taper structure 62 exhibits strong electric field enhancement at the subwavelength aperture as compared with the hollow-HDPE taper structure 61 shown in FIG. 15A. The input terahertz radiation at the entrance aperture of the metal-coated hollow-polymer taper is guided inside the taper without losing too much energy of the terahertz radiation due to structure resonance and leakage.

Therefore, by coating a metal on the hollow-polymer taper structure, the metal-coated hollow-polymer tapers structure may have the ability to confine the terahertz signal, or an input bean, via subwavelength aperture to achieve the subwavelength resolution terahertz images while performing the nearfield image scan by the electronically controlled beam deflector. In some embodiments, the metal coated on the hollow-polymer taper is silver or any other metal that can achieve the same effect as mentioned above.

To perform subwavelength resolution scanning on the surface of the target, the present disclosure provides several means as follows to drive or bend the near-field terahertz radiation of the subwavelength aperture.

Figure 16:
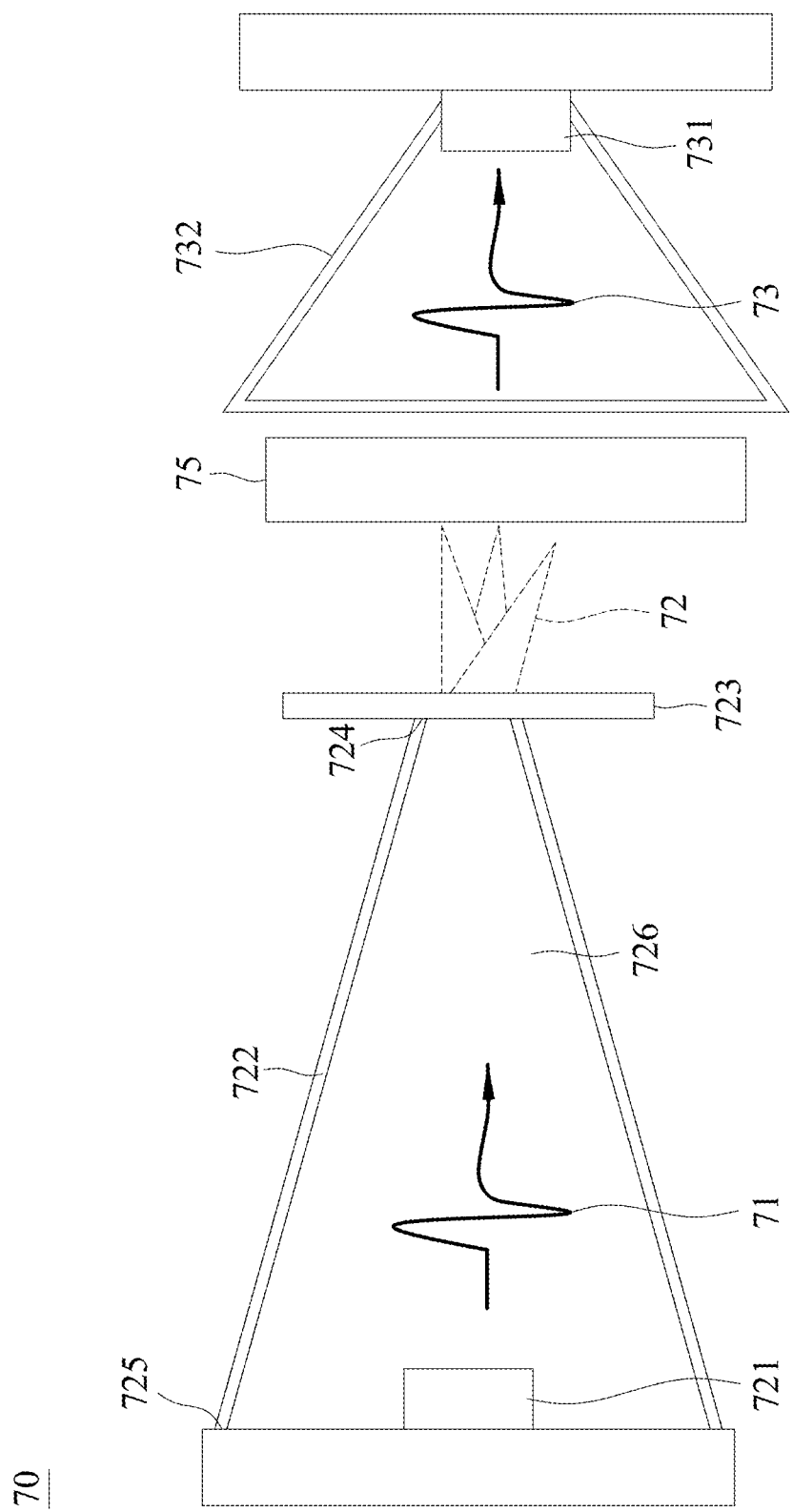
FIG. 16 is a schematic diagram of a device according to an embodiment of the present disclosure.

FIG. 16 shows an embodiment of a device 70 of the present disclosure. The electro-optic beam deflector may be made of tunable metamaterial or metasurface (such as the design of the beam deflector 110 or 120 shown in FIGS. 20-22) and fabricated on a thin substrate to form a beam deflector module 723 of the device 70 (as the beam deflector module 23 shown in FIG. 2), in which the thin substrate has extremely low absorption at the interested terahertz frequencies. A THz source 721 is covered by a taper structure 722 at an entry aperture 725 side to emit a terahertz signal 71. The beam deflector module 723 is attached at an emitting aperture 724 of the taper structure 722, so that the leaving terahertz signal 72 emitted from the emitting aperture 724 may be transmitted through the beam deflector module 723 arranged perpendicular to the direction of the terahertz signal 71 and impact on the target 75 located between the THz source 721 and a THz detector 731. The leaving terahertz signal 72 then reflected from a surface of the target 75 as a reflected terahertz signal 73. The reflected terahertz signal 73 is eventually collected by the taper structure 732 and received by the THz detector 731.

The bean deflector module 723 of some embodiments is fabricated using the electrically controlled phase-changing materials. The direction of the terahertz signal does not change when there is no voltage applied to the beam deflector module 723. When the beam deflector module 723 fabricated with phase-changing material is controlled by the applied bias voltage, the phase front of the propagating wave can be tilted, so that the direction of the terahertz beam can be steered, focused, or collimated.

Figure 17:
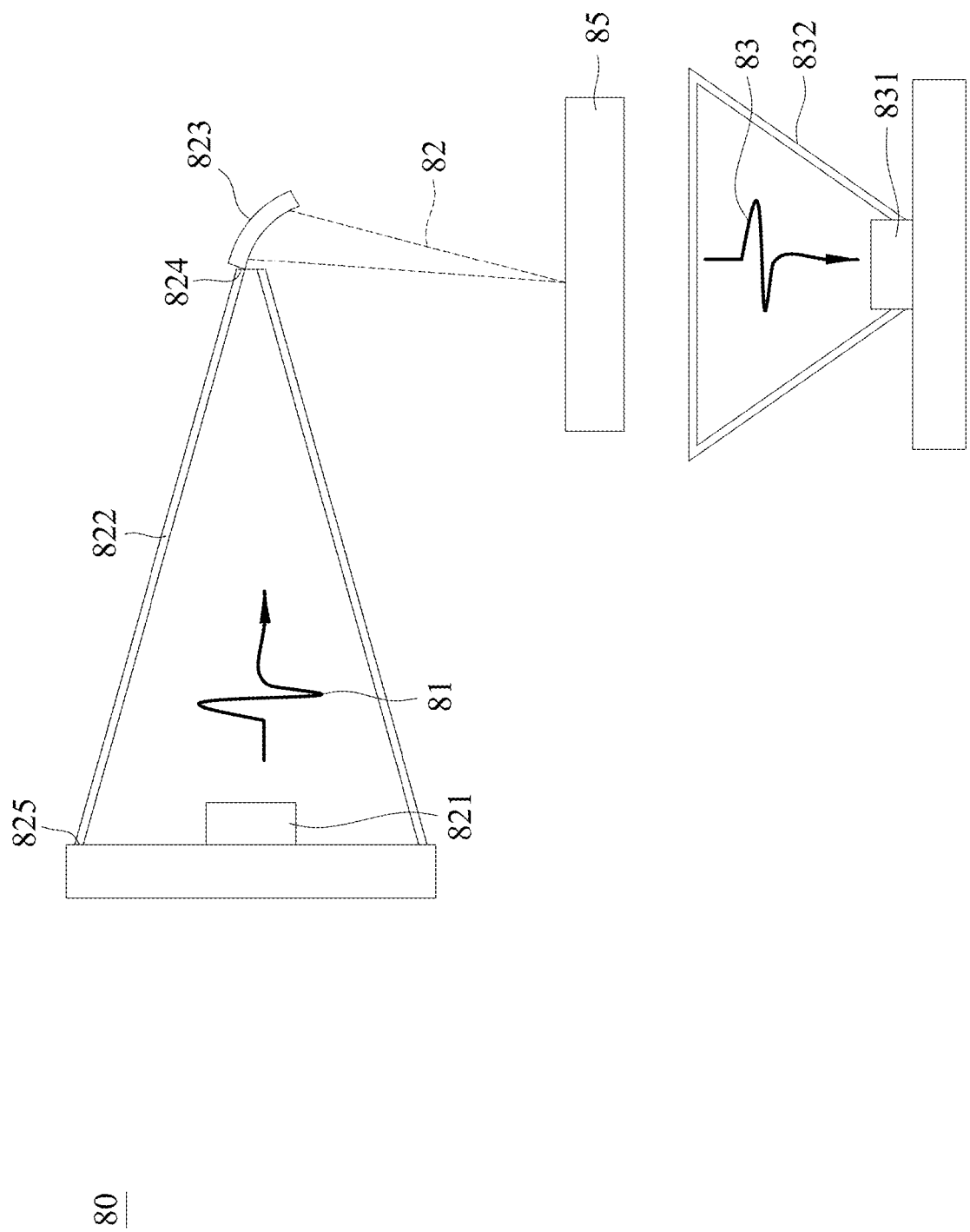
FIG. 17 is a schematic diagram of a device according to the other embodiment of the present disclosure.

FIG. 17 illustrates an embodiment of a device 80 of the present disclosure. The electro-optic beam deflector may be made of tunable metamaterial or metasurface (such as the design of the beam deflector 110 or 120 shown in FIGS. 20-22) and fabricated on a curved surface to form a beam deflector module 823 which may focus and deflect a terahertz signal 81. A THz source 821 is covered by a taper structure 822 at an entry aperture 825 side to emit a terahertz signal 81. In some embodiments, the beam deflector module 823 is partially attached to an emitting aperture 824 of the taper structure 822, so that the terahertz signal 81 leaving from the emitting aperture 824 may be focused and deflected by the beam deflector module 823 and impact on the target 85, which is not necessary to be located between the THz source 821 and a THz detector 831. The focused terahertz signal 82 then reflected from a surface of the target 85 as a reflected terahertz signal 83. The reflected terahertz signal 83 is eventually collected by the taper structure 832 and received by the THz detector 831.

In at least one embodiment, the beam deflector module 823 works like a curved electro-optic mirror surface that may focuse, collimate, diverge, and/or deflect the terahertz signal on an optical axis when the applied bias voltage on the beam deflector module 823 varies. In some embodiments, the refractive index of the electro-optic material of the beam deflector module 823 may change with the applied bias voltage on the beam deflector module 823. Accordingly, the reflection angle of the terahertz signal incident on the electro-optic surface may be varied, and the terahertz signal may be focused at the off-axis of the electro-optic mirror.

Figure 18:
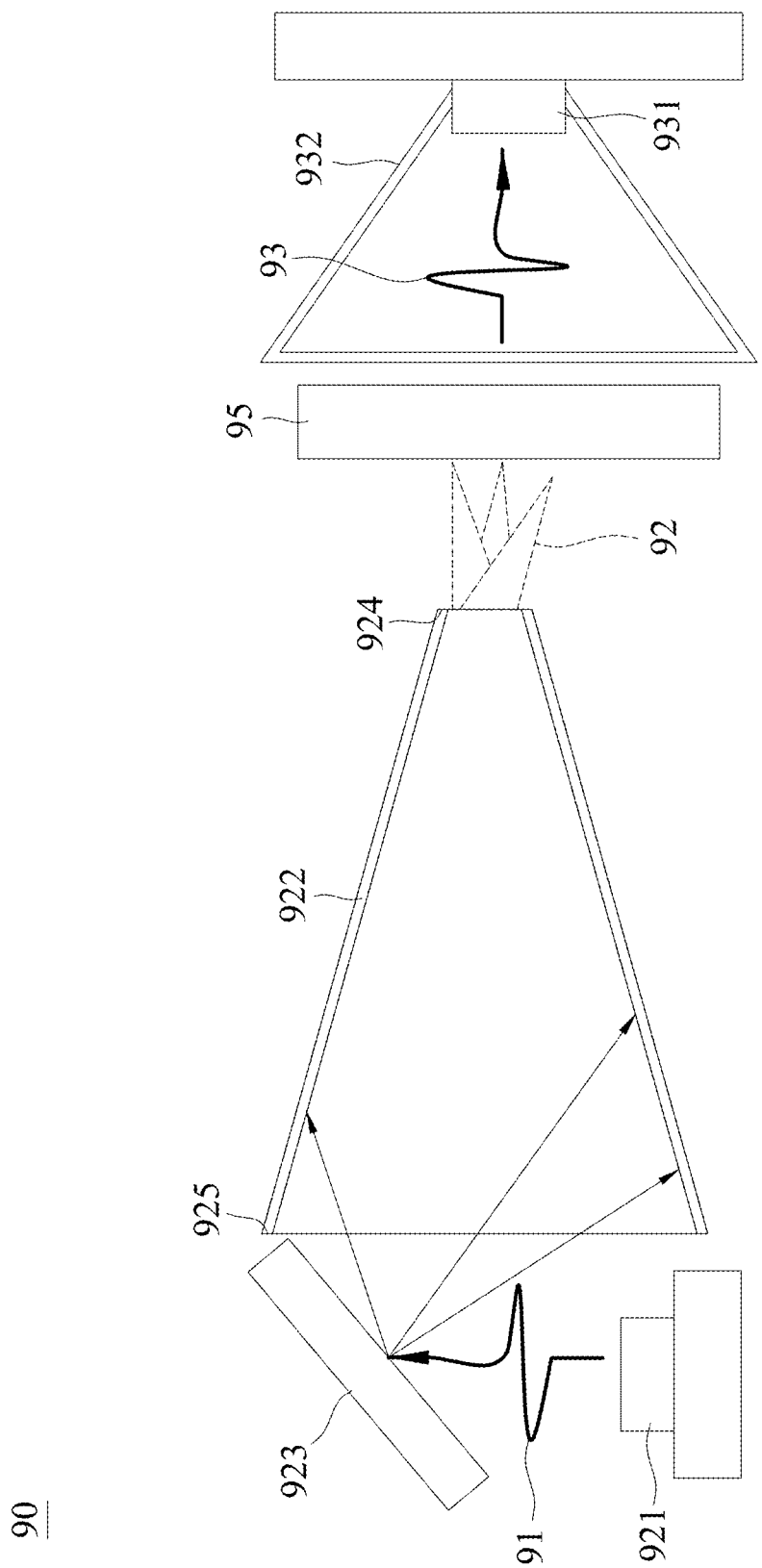
FIG. 18 is a schematic diagram of a device according to another embodiment of the present disclosure.

Referring to FIG. 18, it shows an embodiment of a device 90 of the present disclosure. A beam deflector module 923 is similar with the beam deflector module 823 but not formed on a curved surface. Also, the beam deflector module 923 may be made of tunnable metamaterial or metasurface (such as the design of the beam deflector 110 or 120 shown in FIGS. 20-22). Instead, the beam deflector module 923 is formed on a flat surface. ATHz source 921 of the device 90 is not covered by an entry aperture 925 of a taper structure 922, and the beam deflector module 923 is not attached to an emitting aperture 924 of the taper structure 922. A terahertz signal 91 emitted from the THz source 921 impacts on the beam deflector module 923 at a fixed angle, and a reflection angle of the terahertz signal 91 may be controlled by the beam deflector module 923 based on the applied bias voltage on the beam deflector module 923. In some embodiments, the beam deflector module 923 may comprise an electro-optic beam deflector or a galvo-mirror.

Therefore, the angle of incidence of the reflected terahertz signal 91 enters the aperture 925 of the taper structure 922 is varied and then emits as leaving terahertz signal 92 out from the emitting aperture 924 of the taper structure 922 to impact on the target 95. The leaving terahertz signal 92 is then reflected from a surface of the target 95 as a reflected terahertz signal 93. The reflected terahertz signal 93 is eventually collected by a taper structure 932 and received by a THz detector 931. The arrangements of the device 90 mentioned above can change the incidence angle of the terahertz signal 91 entering the taper structure 922, so that the reflection angles thereof may be changed inside the taper structure 922.

Figure 19:
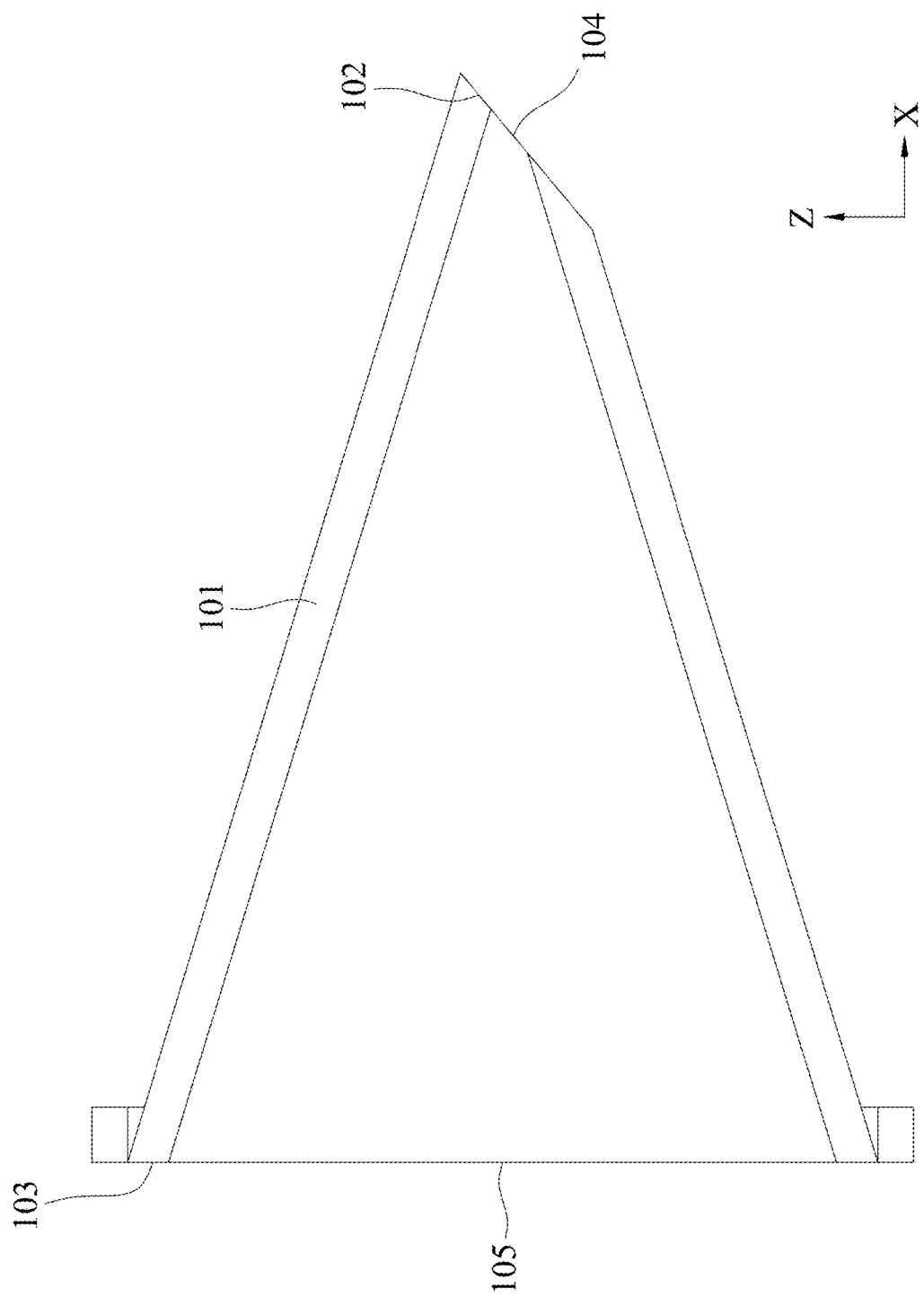
FIG. 19 is a schematic diagram of a taper structure with an inclined-cut on an emitting aperture according to an embodiment of the present disclosure.

FIG. 19 shows an embodiment of the taper structure 101 with an inclined-cut on the emitting aperture 102 of the present disclosure. To achieve the scanning of nearfield terahertz radiation, the emitting aperture 102 of a taper structure 101 may be cut with a certain angle to increase a deflection angle, such that a surface 104 of the emitting aperture 102 is inclined relative to a surface 105 of an entry aperture 103 of the taper structure 101. The terahertz signal leaves the emitting aperture 102 with the inclined-cut in a different direction due to the changes in the reflection angle/anti-resonant reflection pattern inside the taper structure 101.

Figure 20:
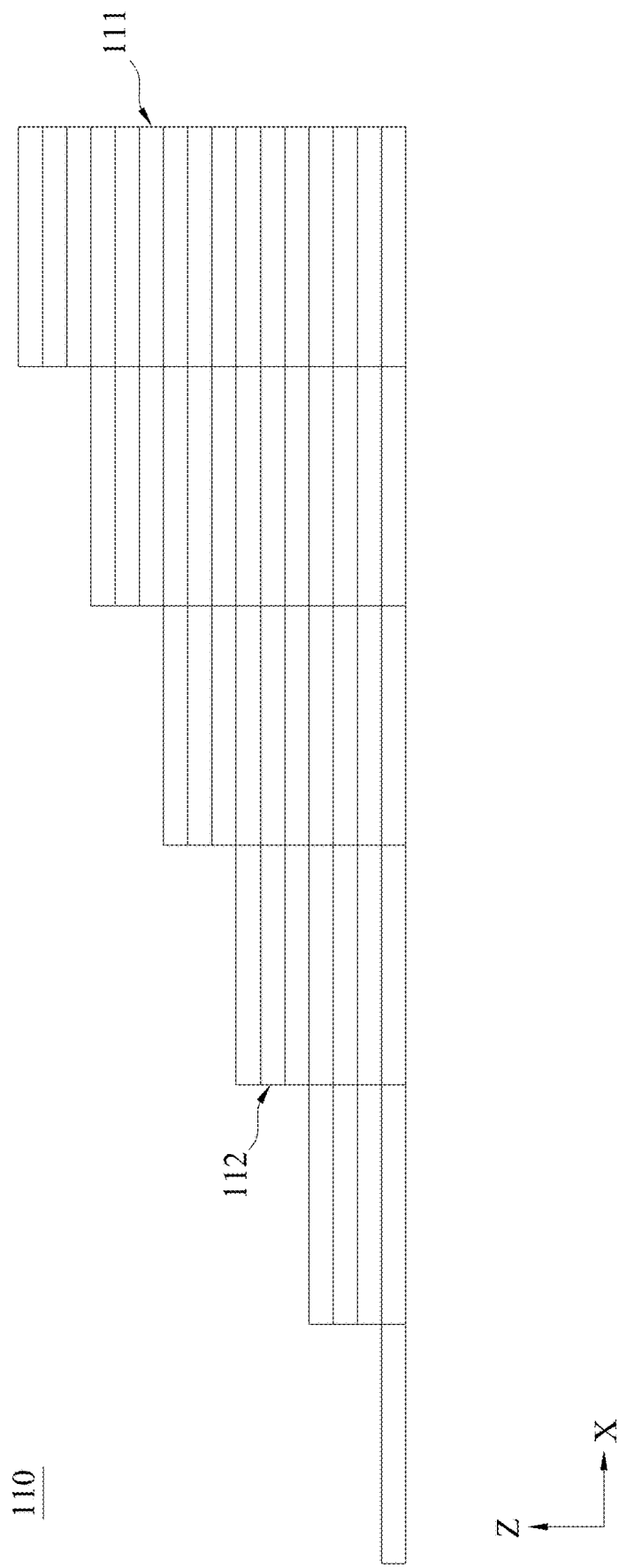
FIG. 20 is a schematic diagram of a physical terahertz fishnet metamaterial (TFMM) prism design of a beam deflector according to an embodiment of the present disclosure.

FIG. 20 illustrates an embodiment of a physical terahertz fishnet metamaterial (TFMM) prism design of a beam deflector 110 of the present disclosure. The physical prism design of a beam deflector 110 may be one of the electro-optic modulator designs in the beam deflector module 723, 823, or 923 shown in FIGS. 16-18. The beam deflector 110 is a TFMM prism for beam steering purpose similar to a regular prism design, except that the fishnet is an anisotropic material which only allows normally incident beams (e.g., an incident terahertz signal). In some embodiments, for the sake of creating a large optical path difference (OPD) to achieve a larger angle beam steering, the beam deflector 110 may be formed as a TFMM prism with a plurality of fishnet layers 111 stacked together to form a plurality of steps 112, and each of the plurality of steps 112 may be formed by at least three of the fishnet layers 111. Accordingly, the beam bending may be achieved by the optical path length difference due to a relative geometry change (or thickness) between the adjacent steps 112. The angle and uniformity of the output beam profile may depend on the number of the fishnet layers 111, the relative geometry between the steps 112, and/or the operating frequency.

Figure 21:
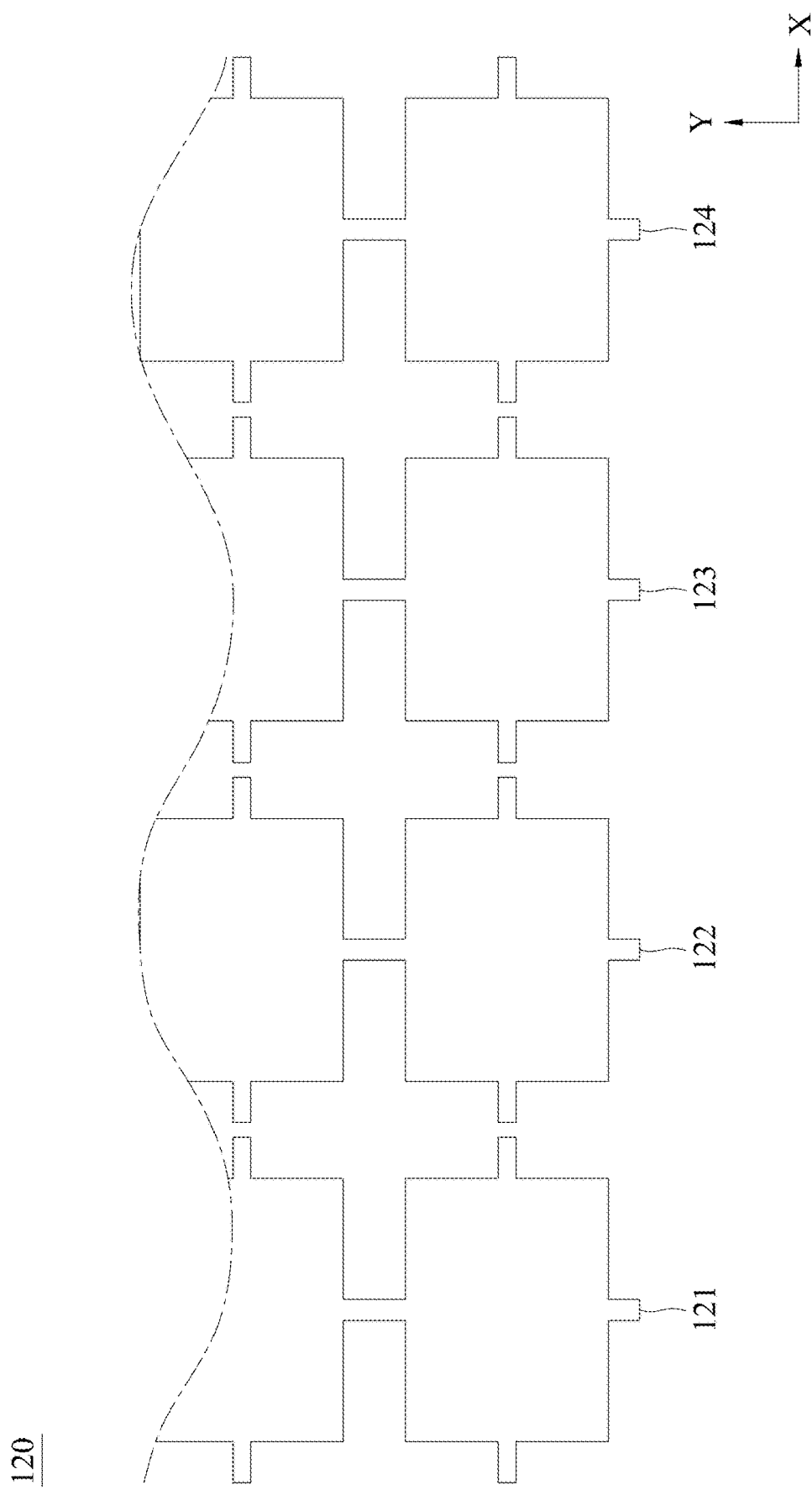
FIG. 21 is a schematic diagram of a flat TFMM prism design of a beam deflector according to an embodiment of the present disclosure.

Referring to FIG. 21, it shows an embodiment of a flat TFMM prism design of a beam deflector 120 of the present disclosure. The flat prism design of a beam deflector 120 may be one of the proposed electro-optic modulator designs in the beam deflector module 723, 823, or 923 shown in FIGS. 16-18. In at least one embodiment, the challenge of fabricating a multilayer TFMM prism may be alleviated with a flat prism structure by combining the concept of beam steering based on the OPD and the large refractive index change of metamaterial near its resonant frequency. For instance, a beam deflector 120 may be fabricated as an array of single layer terahertz fishnet metamaterial structure as shown in FIG. 21. To create a large OPD varied along the direction perpendicular to incident beam, one can apply different external fields to each of the fishnet rows (i.e., fishnet rows 121, 122, 123, and 124), which are not connected with each other. It is thus not necessary to make the beam deflector 120 in a physical prism shape to steer the beam, if the material can create a large ODP varying along the direction perpendicular to the incident beam, such as a terahertz signal.

Figure 22:
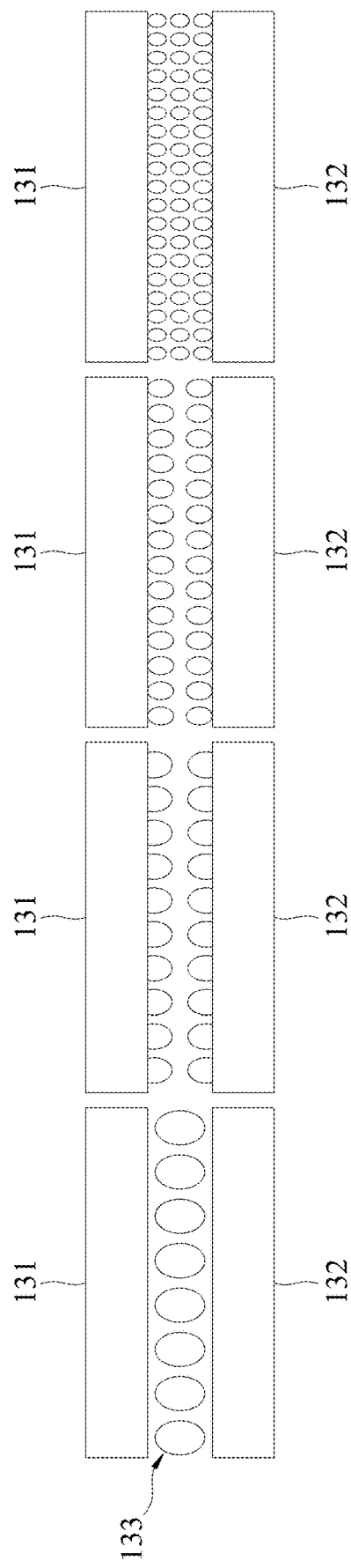
FIG. 22 is a cross section view of droplets of different sizes disposed between two layers of the fishnet rows of a beam deflector according to an embodiment of the present disclosure.

FIG. 22 shows another embodiment to create an electro-optic modulator design of the beam deflector module 723, 823, or 923 shown in FIGS. 16-18. FIG. 22 shows a cross section view of an embodiment of droplets 133 of different sizes disposed between two layers of the fishnet rows. With this design, the flat prism 120 shown in FIG. 21 can be generated due to droplet size induce refractive index changes among different cells including an upper fishnet layer 131, a bottom fishnet layer 132, and a plurality of droplets 133. For example, each of the fishnet rows (i.e., fishnet rows 121, 122, 123, 124) as shown in FIG. 21 may comprises the upper fishnet layer 131 and the bottom fishnet layer 132. A plurality of droplets 133 may be disposed between the upper fishnet layer 131 and the bottom fishnet layer 132. In some embodiments, the plurality of droplets 133 may be formed as a droplet layer, and the number of the droplet layers between the upper fishnet layer 131 and the bottom fishnet layer 132 may depend on the size of the droplets 133 (e.g., the smaller the size of the droplets 133, the more droplet layers). Hence, a gradient refractive index structure may be constructed by varying the droplet size between each of the fishnet rows of the disconnected TFMM array. In some embodiments, the droplets 133 may be composed of a liquid crystal (LC) material, and the size of the LC droplets 133 may be controlled by ultraviolet (UV) radiation to determine the index of refraction gradient.

In some embodiments, the droplet size of the polymer-dispersed liquid crystal (PDLC) may be controlled by a gray scale mask to form gradient structure. With assistance from the fishnet structure, the effective index of refraction can be enlarged. Since TFMM can create large refractive index changes, the fishnet structure of the beam deflector may be used as individual electrodes to apply separate electric fields onto the PDLC, resulting in a refractive index gradient along the direction perpendicular to incident beams, which is equivalent to a real prism.

The conventional lens shaped with different curves can be operated in positive refractive index, but it may be constrained by the diffraction limit. The gradient flat lens infiltrated with materials such as non-uniform LC cells can create an optical effect like a triangular shape prism, but it may be limited by the refractive index of the materials. At least one embodiment of the present disclosure thus provides an actively controlled metamaterial lens of a beam deflector that can overcome these problems by transforming the lens to perform different functions, such as going from focusing to diverging to collimating or to achieve near field or subwavelength focusing by altering the applied voltage. In some embodiments, a beam deflector is designed by using a UV curable PDLC as a dielectric substrate, and the material exposed at different intensities of UV may force the LC droplets inside the polymer to form in different sizes.

Since the ordinary and extraordinary refractive indices of PDLC may be changed according to the average size of the liquid crystal droplets inside the polymer host medium, the material may be exposed at a constantly increasing dosage to achieve the effect of a prism. In some embodiments, based on the above concept, the beam deflector may be fabricated as a tunable flat lens, a prism with active steering, or an even more complicated lens design depending on the configuration of the PDLC substrate.

Figure 23:
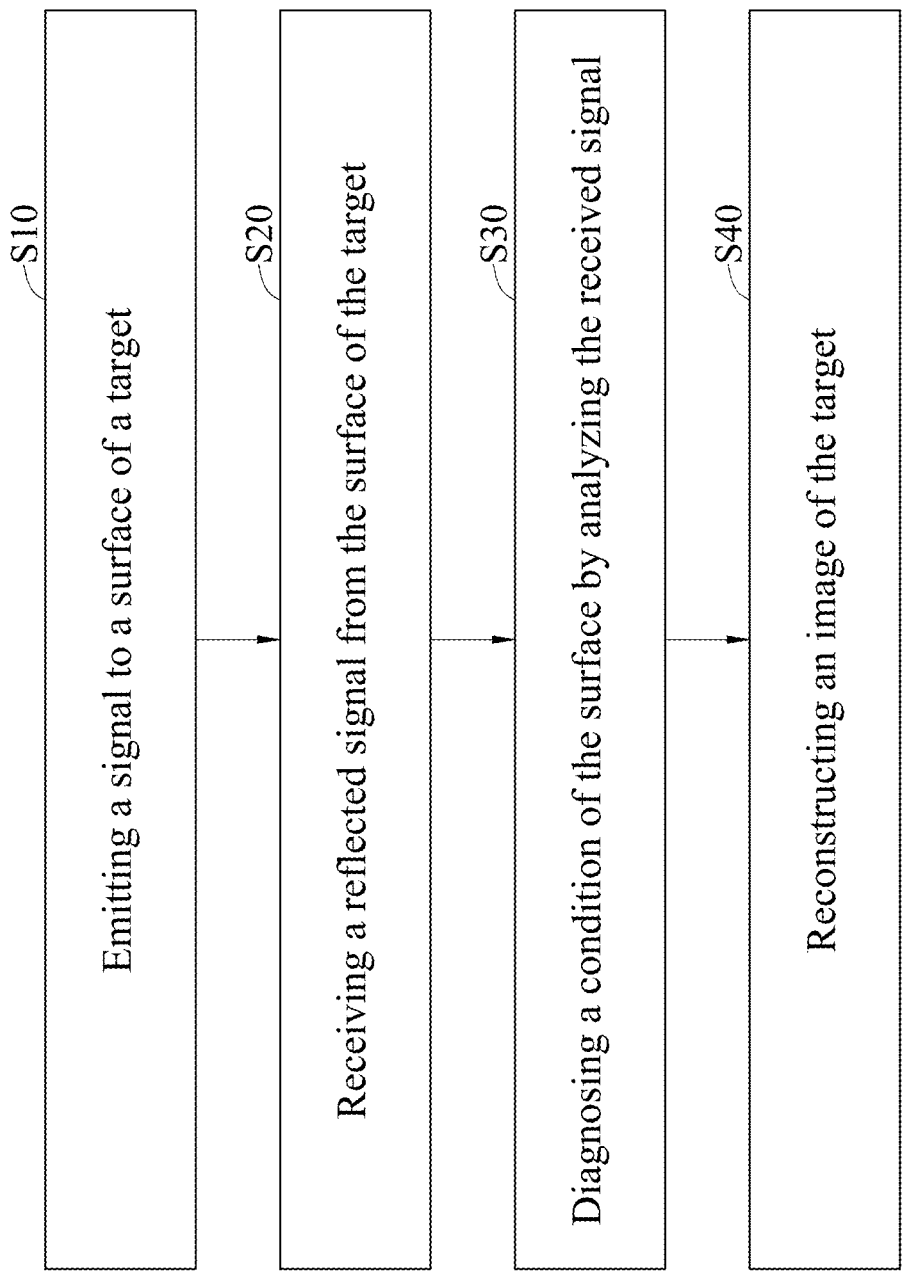
FIG. 23 is a flow chart of processes for operating the portable THz imaging device according to an embodiment of the present disclosure.

FIG. 23 illustrates a flow chart of processes for operating the portable THz imaging device of the present disclosure.

First, in step S10, a generator connected to a THz emitter to induce the THz emitter to emit a terahertz signal to a surface of a target. Second, in step S20, a receiver receives the terahertz signal reflected from the surface of the target. After that, in step S30, the portable THz imaging device may diagnose a condition of the surface of the target by analyzing the received terahertz signal. Finally, in step S40, an image of the target may be reconstructed.

In at least one embodiment, the target of the subject diagnosed by the portable THz imaging device may be a tooth of a patient, and the surface of the target may be an enamel surface of the teeth. In some embodiments, the diagnosing with the portable THz imaging device may be performed by scanning in series of the left buccal, left occlusal, labial, incisal, right buccal, right occlusal and lingual from left side back to right side by reference to the midline of mouth.

In some embodiments, the diagnosed condition of the teeth may be an early detection of dental caries, demineralization enamel in the teeth, monitoring a curing process of dental composites, and identification of dental abnormalities.

In the portable THz imaging device for diagnosing the conditions of a target of the subject as describe in the present disclosure, the THz imaging device may be manufactured as a simple, portable, real-time, and in vivo THz imaging device for imaging dental tissues. Moreover, the portable THz imaging device is much sufficiently sensitive to detect the early stages of dental caries as comparing with the common X-ray. As such, the THz imaging device of the present disclosure may operate in the density for early detection of dental problems such as imaging enamel thickness at high resolution.

The present disclosure has been described with exemplary embodiments to illustrate the principles, features, and efficacies of the present disclosure, but not intend to limit the implementation scope of the present disclosure. The present disclosure without departing from the spirit and scope of the premise can make various changes and modifications by a person skilled in the art. However, any equivalent change and modification accomplished according to the disclosure of the present disclosure should be considered as being covered in the scope of the present disclosure. The scope of the disclosure should be defined by the appended claims.

What is claimed is:

1. A scanning based terahertz(THz) imaging device, comprising:
   a THz emitter for emitting a terahertz signal upward direction, comprising:
   a first cover;
   a first taper structure with multiple layers coated sidewalls disposed in the first cover
   and having a distal end and a proximal end opposed to the distal end;
   a THz source disposed in the first cover and covered by the first taper structure to guide
   and generate a focused near field beam profile at the distal end; and
   a beam deflector module coupled to the first cover and configured to deflect or modulate
   the terahertz signal for scanning;
   a radiation antenna integrated and coupled with the THz emitter and configured for inducing the THz emitter to emit the terahertz signal; and
   a receiver for receiving the terahertz signal, comprising:
   a second cover;
   a second taper structure disposed in the second cover;

a THz detector with a receiving antenna disposed in the second cover and covered by
the second taper structure with multiple layers coated sidewalls, wherein the THz detector is covered by a smaller aperture of the second taper structure, and a bigger aperture of the second taper structure is directed to a top surface of the second cover towards a target.

2. The scanning based THz imaging device of claim 1, wherein the THz source comprising:
a resonant tunneling diode(RTD) with an emitter and a collector;
a resonator antenna electrically connected to the emitter and the collector of the RTD; and
a radiator antenna disposed over the resonator antenna separated by a dielectric layer.

3. The scanning based THz imaging device of claim 2, wherein the RTD is a TBRTD or a multi-barrier RTD comprising a quantum well/barrier/well layers of semiconductor material with non-uniform thickness and material composition, and wherein the TBRTD or the multi-barrier RTD is configured to improve overall DC-RF conversion efficiency and smaller peak current-voltage.

4. The scanning based THz imaging device of claim 2, wherein the radiator antenna stacked on the dielectric layer is a tunable fractal antenna structure configured to change a frequency shift by a reconfiguration of a fractal pattern of the tunable fractal antenna structure or by a voltage induced dielectric constant change of the dielectric layer in the radiator antenna.

5. The scanning based THz imaging device of claim 1, wherein the first taper structure with multiple layers coating sidewalls has an air-core part to minimize a transmission loss of the terahertz signal and enhance a THz signal localization, an emitting aperture, and an entry aperture.

6. The scanning based THz imaging device of claim 5, wherein the air-core part has an inner wall coated with a material of metal to guide and generate the focused beam at a nearfield distance at the emitting aperture of the first taper structure.

7. The scanning based THz imaging device of claim 5, wherein the emitting aperture of the first taper structure is cut with an angle to increase a deflection angle.

8. The scanning based THz imaging device of claim 5, wherein the beam deflector module is disposed at the emitting aperture of the taper structure and configured for the terahertz signal to transmit and manipulate an emitting optical axis of the THz beam.

9. The scanning based THz imaging device of claim 5, wherein the beam deflector module is fabricated on a curved surface for focusing and deflecting the terahertz signal at a nearfield distance, and the beam deflector module is disposed at the emitting aperture of the first taper structure.

10. The scanning based THz imaging device of claim 5, wherein the beam deflector module is disposed at the entry aperture of the first taper structure and configured to deflect the terahertz signal emitted from the THz emitter and therefore changes an entrance angle to enter the taper structure.

11. The scanning based THz imaging device of claim 10, wherein the beam deflector module comprises an electro-optic beam deflector or a galvo-mirror.

12. The scanning based THz imaging device of claim 1, wherein the beam deflector module is a physical terahertz fishnet metamaterial prism having a stacked fishnet structure.

13. The scanning based THz imaging device of claim 1, wherein the beam deflector module is a flat terahertz fishnet metamaterial prism having an array of a single layer terahertz fishnet metamaterial structure.

14. The scanning based THz imaging device of claim 13, wherein the terahertz fishnet metamaterial structure comprises:
a first layer;
a second layer opposed to the first layer;
a plurality of droplets disposed between the first layer and the second layer to form a plurality of droplet layers.

15. The scanning based THz imaging device of claim 14, wherein the droplets is composed of a liquid crystal material, and a size of the droplets is controlled by ultraviolet radiation to create different refractive indices.

16. The scanning based THz imaging device of claim 1, wherein the beam deflector module is an actively-controlled metamaterial lens/beam deflector for transforming functions between focusing function, diverging function, collimating function, beam deflection, or any combination of two or more functions by altering an applied voltage among metamaterial array.

17. The scanning based THz imaging device of claim 1, further comprising a connector for detachably connecting the THz emitter to the receiver and separating the THz emitter from the receiver with a distance.

18. The scanning based THz imaging device of claim 17, the connector is configured to adjust the distance between the THz emitter and the receiver.

19. A method for diagnosing a disease, disorder, or condition of a subject, comprising:
providing the scanning based THz imaging device of claim 1;
emitting a terahertz signal from a THz emitter to the target in the subject in need thereof;
receiving the terahertz signal reflected from the target by a receiver; and
diagnosing a condition of the target by analyzing the received terahertz signal.

20. The method of claim 19, further comprising reconstructing an image of the target.

21. The method of claim 19, wherein the target is dielectric material with or without water content.

22. The method of claim 19, wherein the disease, disorder, or condition of a subject is selected from the group consisting of dental caries, demineralization of teeth, peri-implantitis, periodontal disease, gingivitis, a curing process of dental composites, a lesion in the oral structure, dental abnormalities, burns, edema, and cancer.

23. A method for imaging a target in a subject, comprising:
providing the scanning based THz imaging device of claim 1;
emitting a terahertz signal from a THz emitter to a surface of the target in the subject in need thereof;
receiving the terahertz signal reflected from the surface of the target by a receiver; and
reconstructing an image of the subject by the received terahertz signal.

24. The method of claim 23, wherein the target is dielectric material with or without water content.

* * * * *